(12) United States Patent
Jensen et al.

(10) Patent No.: US 8,933,063 B2
(45) Date of Patent: Jan. 13, 2015

(54) PREPARATION OF A CRYSTALLINE ANTIBIOTIC SUBSTANCE

(75) Inventors: Jan Jensen, Kokkedal (DK); Niels Rastrup Andersen, Vanløse (DK)

(73) Assignee: Leo Pharma A/S, Ballerup (DK)

( * ) Notice: Subject to any disclaimer, the term of this patent is extended or adjusted under 35 U.S.C. 154(b) by 1562 days.

(21) Appl. No.: 12/084,231

(22) PCT Filed: Oct. 30, 2006

(86) PCT No.: PCT/DK2006/000600
§ 371 (c)(1),
(2), (4) Date: Aug. 19, 2008

(87) PCT Pub. No.: WO2007/051468
PCT Pub. Date: May 10, 2007

(65) Prior Publication Data
US 2009/0131389 A1    May 21, 2009

Related U.S. Application Data

(60) Provisional application No. 60/731,247, filed on Oct. 31, 2005.

(51) Int. Cl.
*A61K 31/575* (2006.01)
*C07J 13/00* (2006.01)

(52) U.S. Cl.
CPC ................... *C07J 13/007* (2013.01)
USPC .......................................... 514/182; 552/530

(58) Field of Classification Search
USPC ...................... 514/170, 171, 182; 552/530
See application file for complete search history.

(56) References Cited

U.S. PATENT DOCUMENTS 3,072,531 A * 1/1963 Godtfredsen et al. ......... 514/182
6,103,884 A * 8/2000 Koreeda et al. .................. 536/5

FOREIGN PATENT DOCUMENTS

| BE | 619 287 A | 6/1962 |
|---|---|---|
| DE | 14 68 178 A1 | 2/1969 |
| ES | 2 204 331 A1 | 4/2004 |
| ES | 2 206 110 A1 | 6/2004 |
| FR | 1 326 076 A | 5/1963 |
| GB | 999794 | 7/1962 |
| GB | 930 786 A | 7/1963 |
| RU | 2 192 470 C2 | 11/2002 |
| WO | WO 86/03966 A1 | 7/1986 |
| WO | WO 96/03128 A1 | 2/1996 |

OTHER PUBLICATIONS

Terence L. Threlfall (Analysis of Organic Polymorphs, Analyst, Oct. 1995, vol. 120 pp. 2435-2460).*
Hikino et al., "Fungal metabolites. II. Fusidic acid, a steroidal antibiotic from Isaria kogane," Chemical and Pharmaceutical Bulletin, vol. 20, No. 5, 1972, pp. 1067-1069.
International Search Reoprt mailed Jul. 30, 2007, issued in PCT International Application No. PCT/DK2006/000600.

* cited by examiner

*Primary Examiner* — Sabiha N Qazi
(74) *Attorney, Agent, or Firm* — Birch, Stewart, Kolasch & Birch, LLP

(57) ABSTRACT

The present invention relates to processes for the crystallisation and for the preparation and isolation of a novel crystalline form of fusidic acid, to the use of said processes in the manufacture of pharmaceutical formulation or medicament, and to the use of said crystalline fusidic acid form for the treatment of bacterial infections.

22 Claims, 10 Drawing Sheets

PREPARATION OF A CRYSTALLINE ANTIBIOTIC SUBSTANCE

FIELD OF THE INVENTION

The present invention relates to a novel crystalline form of fusidic acid, to its preparation, pharmaceutical compositions containing it, and to the use of said crystalline fusidic acid form as a medicament in treatment of infectious diseases.

BACKGROUND OF THE INVENTION

Fusidic acid [CAS6990-06-3] [Nature, Vol. 193, No. 4819, p. 987, 1962] which can be isolated from the fermentation broth of *Fusidium coccineum* is the most antibiotically active compound of the fusidanes and is the only fusidane used clinically in treatment of infectious diseases. Fusidic acid (Fucidin®) is used clinically for the treatment of severe staphylococcal Infections, particularly in bone and joint Infections, in both the acute and the intractable form of the disease (*The Use of Antibiotics*, 5th Ed., A. Kucers and N.McK. Bennett (Eds.), Butterworth 1997, pp. 580-587, and references cited therein).

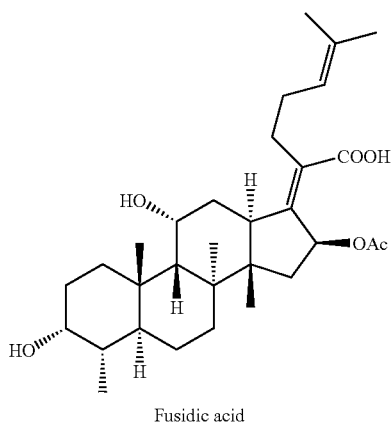

Fusidic acid

Although fusidic acid is most commonly used against staphylococci, it is also used against several other gram-positive species. The clinical value of fusidic acid is also due to its efficient distribution in various tissues, low degree of toxicity and allergic reactions and the absence cross-resistance with other clinically used antibiotics. Fusidic acid is widely used in local therapy for a number of skin and eye infections caused by staphylococci. It is generally given in combination with common antibiotics such as penicillins, erythromycins or clindamycin. It has also been used as an alternative to vancomycin for the control of *Clostridlum diffcile*. Compared to staphylococci, several other gram-positive cocci are often less susceptible to fusidic acid. As an example, streptococcal species are generally up to 100-fold less sensitive to fusidic acid than staphylococci [Kuchers et al; supra]. Other sensitive bacteria include gram-positive anaerobic cocci, such as *Peptococcus* and *Peptostreptococcus* spp., aerobic or anaerobic gram-positive bacteria, such as *Corynebacterium diphtherdae, Clostridium tetani, Clostridium difficile* and *Clostridlum perfringens*. Gram-negative bacteria are resistant except for *Neisseria* spp. and *Legionella pneumophila*. The drug is highly potent against both intracellular and extracellular *M. leprae*.

The solid form, such as the crystal form, of a drug substance or active pharmaceutical ingredient used in a pharmaceutical formulation or medicament is important based on solubility, dissolution rate, hygroscopicity, bioavailability, and stability differences between the different solid forms. Thus the existence of various solid forms, such as polymorphism or pseudo polymorphism can affect the properties of the quality of the drug product.

Hence, a specific crystal form, including solvates and hydrates, might be preferable over another one. Furthermore certain forms may be preferable depending on the specific formulation and/or application. For example, the properties of a drug, such as the dissolution rate of the active ingredient, may be tuned by the proper choice of a certain crystal form, or mixtures thereof.

In a specific commercial pharmaceutical formulation, fusidic acid is presently marketed [see Monographs in the European Pharmacopeia 5.0] as a hemihydrate, which is the only hemihydrate form which has been described.

Patent GB 930,786 discloses salts of fusidic acid with organic and inorganic bases, solvates of fusidic acid, namely a benzene solvate and a methanol solvate. This patent further discloses an unspecified fusidic acid form with IR absorption bands (KBr) at 1265, 1385, 1695, 1730 and 3450 cm$^{-1}$ and having a specific rotation $[\alpha]_D^{22}$ of minus 9 degrees (1% solution in CHCl$_3$) obtainable by crystallisation of the methanol solvate of fusidic acid from ether. However, this form is distinct from the form of the present invention evident from the depicted IR spectrum in GB 930,786 which indicates that this form actually corresponds to the presently marketed hemihydrate form.

Solvates and salts of fusidic acid have also been disclosed in British patent GB 999,794. Patent ES 2208110 discloses two solvent free crystalline forms of fusidic acid called Form I and Form II, and a crystalline hemihydrate called Form III which is identical to the presently marketed hemihydrate, respectively. The crystalline forms were identified and characterised by IR spectroscopy, differential scanning calorimetry, X-ray diffraction and melting points.

Patent WO 96/03128 discloses tablets containing a sodium salt form of fusidic acid and WO 86/03966 describes an ophthalmic gel composition comprising an undefined form of suspended fusidic acid.

SUMMARY OF THE INVENTION

The present invention surprisingly provides a novel crystalline form of fusidic acid and a process for the preparation of said crystalline fusidic acid.

In one aspect, this invention relates to crystalline fusidic acid characterised by exhibiting one or more of the following features a)-k), respectively:
a) a fourier transform (FT-NIR) Raman spectrum exhibiting one or more of the following intensity peaks at approximately 3008, 2937, 2871, 1725, 1707, 1666, 1651, 1468, 1379, 1348, 1195, 1078, 1032, 972, 917, 792, 745, 696, 612, 569, 547, 527, 463, 175, 120, or 86 (±3 cm$^{-1}$), respectively;
b) a fourier transform (FT-NIR) Raman spectrum substantially similar to that shown in FIG. 1;
c) an attenuated total reflectance fourier transform infrared (FTIR-ATR) spectrum exhibiting one or more of the following attenuated total reflectance peaks at approximately 3644, 3489, 2992, 2937, 2871, 1722, 1708, 1442, 1381, 1352, 1283, 1255, 1218, 1204, 1175, 1149, 1109, 1069, 1048, 1028, 962, 941, 917, 851, 828, 791, 750, 690, or 656 (±3 cm$^{-1}$), respectively;

d) an attenuated total reflectance fourier transform infrared (FTIR-ATR) spectrum spectrum substantially similar to that shown in FIG. 2;

e) a near infrared (FT-NIR) spectrum exhibiting one or more of the following absorbance peaks at approximately 10414, 8373, 7115, 6846, 6503, 5824, 4996, 4889, 4831, 4680, 4365, 4306, or 4067 (±5 cm$^{-1}$), respectively;

f) a near infrared (FT-NIR) spectrum substantially similar to that shown in FIG. 3;

g) an X-ray powder diffractogram (XRD) exhibiting one or more of the following angles of reflection 2θ (±0.1) at approximately 7.2, 9.3, 9.9, 12.6, 13.1, 14.3, 14.7, 14.9, 15.4, 16.7, 17.9, 18.1, 18.5, 18.9, 19.5, 20.8, 21.8, 22.7, 23.5, 24.0, 24.4, 25.3, 26.0, 26.6, 26.8, 28.2, 28.9, or 29.7, respectively;

h) an X-ray powder diffractogram (XRD) substantially similar to that shown in FIG. 4;

i) a $^{13}$C CP/MAS solid-state NMR spectrum exhibiting one or more of the following resonances at approximately 173.9, 169.3, 146.1, 137.0, 133.3, 120.6, 76.2, 71.1, 69.1, 49.7, 49.4, 45.0, 39.9, 38.5, 36.9, 35.8, 34.5, 32.7, 30.9, 29.5, 28.0, 26.5, 20.7, 20.0, 18.0, or 16.9 (±0.5) ppm, respectively;

j) a $^{13}$C CP/MAS solid-state NMR spectrum substantially similar to that shown in FIG. 6;

k) one or more of the following single-crystal X-ray diffraction experimental data: crystal system=monoclinic, space group=P21, a [Å]=12.2, b [Å]=8.0, c [Å]=13.9, α [°]=90 β [°]=94, γ [°]=90, cell volume [Å$^3$]=1360, or Z=2, respectively.

In yet another aspect, this invention relates to isolated crystalline fusidic acid of the present invention as defined above which has a polymorphic, purity of at least 80%, such as 81%, 82%, 83%, 84%, 85%, 86%, 87%, 88%, 89%, 90%, 91%, 92%, 93%, 94%, 95%, 96%, 97%, 98%, 99%, or 100%.

In yet another aspect, this invention relates to isolated fusidic acid of the present invention as defined above which has a degree of crystallinity of at least 80%, such as %, 82%, 83%, 84%, 85%, 86%, 87%, 88%, 89%, 90%, 91%, 92%, 93%, 94%, 95%, 96%, 97%, 98%, 99%, or 100%.

In yet another aspect, this invention relates to a mixture or composition of crystalline forms of fusidic acid, including pseudopolymorphs of fusidic acid, comprising crystalline fusidic acid of the present invention as defined above.

In yet another aspect, this invention relates to a mixture or a formulation comprising crystalline fusidic acid of the present invention as described above which further comprises crystalline fusidic acid hemihydrate.

In yet another aspect, this invention relates to the use of fusidic acid of the present invention for the manufacture of fusidic acid hemihydrate.

In yet another aspect, this invention relates to a method for the preparation of crystalline fusidic acid hemihydrate, said method comprising the step of crystallizing fusidic acid of the present invention in a suitable solvent or mixture of solvent.

In yet another aspect, this invention relates to crystalline fusidic acid as defined above for use in therapy.

In yet another aspect, this invention relates to a pharmaceutical composition comprising crystalline fusidic acid as described above together with a pharmaceutically acceptable excipient or vehicle.

In yet another aspect, this invention relates to a method of treating, preventing or ameliorating infections in a patient, the method comprising administering to said patient an effective amount of crystalline fusidic acid as described above, and optionally further comprising concomitant or sequential administration of one or more other therapeutically active compounds.

In yet another aspect, this invention relates to the use of crystalline fusidic acid as described above for the manufacture of a medicament for the treatment, amelioration or prophylaxis of infections.

In yet another aspect, this invention relates to the use of crystalline fusidic acid fusidic acid as described above for controlling microbial growth.

In yet another aspect, this invention relates to the use of crystalline fusidic acid according as described above for the prevention or prophylaxis of bacterial infections during animal breeding.

In yet another aspect, this invention relates to a method for the preparation of crystalline fusidic acid as described above, said method comprising the step of desolvating fusidic acid hemihydrate, e.g. in a suitable solvent or mixture of such solvents.

In yet another aspect, this invention relates to a method for the preparation of crystalline fusidic acid as described above, said method comprising the steps of e) dissolving fusidic acid in acetonitrile, acrylonitrile, adiponitrile, benzonitrile, propanenitrile, or mixtures of said solvents, optionally with heating;

f) cooling or concentrating of the solution obtained in step a);

g) allowing crystalline fusidic acid of the present invention to crystallise;

h) isolating the crystalline fusidic acid of the present invention.

In yet another aspect, this invention relates to a method for the preparation of crystalline fusidic acid as described above, said method comprising the steps of j) mixing fusidic acid with a solvent in which of crystalline fusidic acid of the present invention as described above is essentially insoluble or sparingly soluble;

k) storing or stirring of the mixture obtained in step j) optionally with heating followed by cooling, until a suspension is obtained in which the suspended crystals essentially consist of crystalline fusidic acid of the present invention as described above;

l) isolating the crystalline fusidic acid as described above from the suspension.

In yet another aspect, this invention relates to method of preparing a pharmaceutical formulation, said method comprising the step of mixing fusidic acid according to any one of claims as above with a pharmaceutical acceptable excipient or carrier.

DETAILED DESCRIPTION OF THE INVENTION

Figure 1:
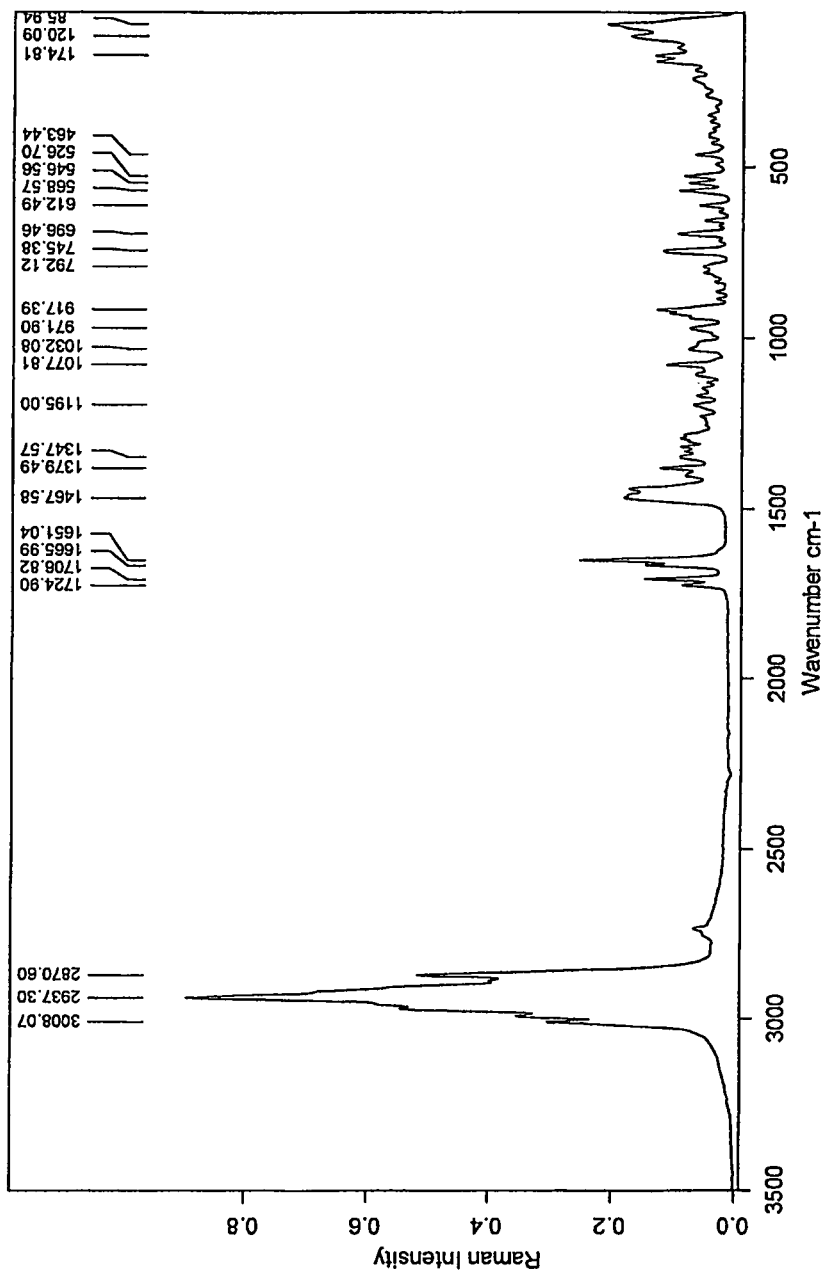
FIG. 1 is a graph showing the Raman spectrum (FT-NIR-Raman) of the crystalline fusidic acid of the present invention. The Y-axis shows the Raman intensity and the X-axis the wavenumber (cm$^{-1}$).

Crystallisation is a well known technique for the purification of chemical compounds and for obtaining a desired crystalline form of chemical compounds. However, it is known that the crystallisation of polymorphs is affected by a number of effects and the mechanism of these effects is not known and the quantitative relationship between the operational factors and the crystallisation characteristics of the polymorphs is not clearly understood.

The crystallisation process of polymorphous crystals is composed of competitive nucleation, growth, and the transformation from a metastable to a stable form. To selectively crystallise polymorphs, the mechanism of each elementary step in the crystallisation process needs to be in clear relation to the operational conditions and the key controlling factors [Crystal Growth & Design, 2004, Vol. 4, No. 6, 1153-1159].

It is presently believed that the novel crystalline non-solvated and anhydrous form of fusidic acid of the present invention as described above represents a thermodynamically more stable polymorphic form. Thermodynamically more stable crystal forms of drug products are generally preferred since they do not transform to other crystal forms during the manufacturing process or in the final drug formulation [Topics in Current Chemistry, Vol. 198, 1998, 164-208].

In a comparative six month standard stability study commonly used for active pharmaceutical ingredients with known forms of fusidic acid, including the presently marketed hemihydrate, the fusidic acid form of the present invention was shown to be the most stable form:

TABLE 1

Stability assay (after 6 month storage at 40° C.) for different polymorphic forms of fusidic acid

| Crystal form | HPLC-assay[a] (% of origin) | Impurities total (%) |
|---|---|---|
| Fusidic acid of the present invention | 99.2 | 0.1 |
| Fusidic acid hemihydrate | 87.7 | 8.7 |
| Fusidic acid form I from ES 2208110 | 98.2 | 1.0 |
| Fusidic acid form II from ES 2208110 | 88.2 | 5.2 |

[a]Column: LiChrospher 100 RP-18.5 µm, 125 × 4 mm, Mobile phase: MeCN:MeOH:0.05 M H$_3$PO$_4$ (60:10:30), Flow rate: 1.2 ml/min, Detector wavelength: 235 nm, Column oven: 25° C., Injection volume: 10 µl Raw fusidic acid, such as fusidic acid of technical grade, may be prepared by methods well known in the literature through fermentation. Methods for the preparation of fusidic acid and its isolation and purification have been described earlier, e.g. In patent ES 2204331 or in ES 2208110, in U.S. Pat. No. 3,072,531, in GB 930,786, in Danish patent 99802, by W. O. Godtfredsen et al. in Tetrahedron 1962, Vol 18, pp. 1029-1048 or in Process Biochemistry, December 1969, or in Biotechnology of Industrial Antibiotics, E. J. Vandamme Ed., Marcel Dekker, Inc., New York & Basel 1984, pp 427-449, and references cited therein, all of which are hereby incorporated by reference.

Crystalline fusidic acid hemihydrate may be prepared by dissolving crude or raw fusidic acid in ethanol to give a solution, such as a solution of 20-30% (w:v) of fusidic acid, followed by good mixing of said solution with water at a ratio of 0.9-1.1 via parallel and controlled feeding of both solutions to a container at 23-28° C., such that crystalline particles are generated.

Precipitation and nucleation times may be varied by adjusting the concentration of solute, the rates of flow of solution and the anti-solvent water, and the temperature of the solvent and anti-solvent. The mixture may after complete transfer rest, optionally with mixing, e.g. to complete the crystallisation process or to allow for the growing of the larger crystals at the cost of the smaller ones in order to achieve a preferred crystal size distribution (redissolution). Preferably the solution of fusidic acid is filtered before mixing with the water as this will remove any foreign particles and undesired seeding crystals such as inadvertent seeds. Preferably the solution and the antisolvent are transferred in equal portions relative to each other meaning that the solution and the antisolvent are mixed with essentially constant ratio. The rate at which crystallisation takes place is dependent on the dosing rate. Preferably the transfer of solution and water is continuous and essentially linear. The crystalline fusidic acid hemihydrate particles can be isolated by simple techniques, for example filtration and/or by centrifugation, preferably by filtration. Seeding of the crystallisation mixture may not be necessary to obtain the desired hemihydrate crystals. This may be due to the fact that crystallisation under the conditions above occurs as spontaneous nucleation of the kinetically favoured crystal form. However, seeding with hemihydrate crystals may, depending on the process conditions, be used to improve the physical properties of the hemihydrate crystals, such as crystal size.

The crystalline fusidic acid of the present invention as described above may be prepared by dissolving fusidic acid, such as fusidic acid hemihydrate as described above, either totally, to give a solution, or partly, to give a suspension or slurry, optionally with heating, in an appropriate solvent, such as up to the boiling point of the solvent used. When a solvate or a hydrate is used, the process is referred to as a desolvation process wherein the solvent or the hydrated water is removed. An appropriate solvent includes a solvent which is e.g. capable of dissolving said fusidic acid hemihydrate, or another form of the starting fusidic acid respectively, and in which the crystalline fusidic acid of the present invention as described above is essentially insoluble or sparingly soluble. The suspension or solution may be further heated or kept at the elevated temperature after the dissolution process depending on the solvent used. This may ensure that, e.g. if a suspension was obtained, that the transformation to the anhydrous fusidic acid form of the present invention may complete faster. Depending on the solvent used and the temperature, the crystalline fusidic acid of the present invention may precipitate from the solution, or, after a certain time, the suspended crystals may essentially consist of the fusidic acid form of the present invention. Typically transformation, or desolvation respectively, may be completed after 3-4 hours in mixtures of alcohols and water, such as methanol or ethanol and water, at 50° C., or after 2-3 hours in the same mixtures at 60° C. or 70° C. Cooling or solvent evaporation might be used to induce precipitation or to enhance the yield of the product, which can be isolated for example by filtration.

Furthermore the crystalline fusidic acid of the present invention may be prepared by crystallisation from a suitable solvent, such as a solvent selected from the list consisting of acetonitrile, acrylonitrile, adiponitrile, benzonitrile, and propanenitrile, or mixtures of said solvents, wherein fusidic acid is dissolved, usually with heating, such as to the boiling point of said solvents and wherein the crystalline fusidic acid of the present invention crystallises, usually after cooling of the solution, such as to ambient temperature, e.g. to 5-30° C., e.g. 10-15° C., e.g. 20-25° C., or after concentrating the solution, e.g. by solvent evaporation. Since the fusidic acid is usually essentially dissolved before crystallisation process, any solid form or crystal form of fusidic acid may be used as the starting material, including but not limited to all polymorphs, solvates, or mixtures thereof described in this application or the references cited herein.

Furthermore the crystalline fusidic acid of the present invention may be prepared by mixing fusidic acid, including any polymorph, or mixtures thereof, with a solvent in which of crystalline fusidic acid of the present invention as described above is essentially insoluble or sparingly soluble, such as water, ethanol, a mixture of methanol and water, acetonitrile, ethyl formate, or mixtures of said solvents.

The mixture may either be a solution or a suspension depending on the solubility of the starting solid form, the amount of solvent (concentration) and/or the temperature. With time, e.g. upon storing, preferably with stirring, the thermodynamically more stable crystal form of the present invention may form, which can be isolated from the suspension by e.g. filtration. The time necessary for complete transformation may vary depending on the temperature, the initial solid form, e.g. crystal form, the solvent, etc. To enhance the crystal transformation, the suspension may be heated, such as to the boiling point of the solvent followed by cooling, such as to ambient temperature, e.g. to 5-30° C., e.g. 10-15° C., e.g. 20-25° C., to increase the amount of the precipitated fusidic acid of the present invention, which may be filtered off.

Instead of heating and cooling, crystallisation may be achieved by concentrating a dilute solution anywhere above to a concentration at which crystallisation occurs.

Mixtures of one or more crystalline forms of the same pharmaceutically active ingredient may advantageously be used in order to achieve a certain release profile from a formulation due to variations of the solubilities and the dissolution profiles of the various crystal forms. Hence, the physico chemical properties, such as the bioavailability of a formulation may be tuned by appropriate mixing of various crystal forms in order to accomplish a composition with optimised properties, such as for sustained release formulations.

Embodiments

In a more specific aspect, this invention relates to a mixture of crystalline forms of fusidic acid, comprising crystalline fusidic acid of the present invention as described above, wherein the mixture of crystalline forms of fusidic acid essentially consists of crystalline fusidic acid hemihydrate.

In yet another more specific aspect, this invention relates to a mixture of crystalline forms of fusidic acid, comprising crystalline fusidic acid of the present invention as described above, wherein the mixture of crystalline forms of fusidic acid comprises crystalline fusidic acid characterised by exhibiting one or both of the following features t) or u):

t) an infrared (FT-IR) spectrum (KBr) having one or more significant bands at approximately 973, 1253, 1377, 1721, or 3559 (±3 $cm^{-1}$), respectively; or u) an X-ray powder diffractogram (XRD) with one or more characteristic intensity peaks exceeding 20% with respect to the largest peak, occurring at 2θ values (±0.1) of approximately 2.1, 6.8, 9.4, 10.4, 11.8, 12.8, 13.7, 14.2, 15.8, 17.3, 18.5, or 22.9, respectively.

In yet another more specific aspect, this invention relates to a mixture of crystalline forms of fusidic acid, comprising crystalline fusidic acid of the present invention as described above, wherein the mixture of crystalline forms of fusidic acid comprises crystalline fusidic acid characterised by exhibiting one or both of the following features v) or w):

v) an infrared (FT-IR) spectrum (KBr) having one or more significant bands at approximately 976, 1255, 1377, 1697, 1721 (±3 $cm^{-1}$), respectively; or w) an X-ray powder diffractogram (XRD) with one or more characteristic intensity peaks exceeding 20% with respect to the largest peak, occurring at 2θ values (±0.1) of approximately 8.8, 11.5, 13.6, 14.4, or 17.4, respectively.

Any mixtures of crystalline forms of fusidic acid, comprising crystalline fusidic acid of the present invention described herein may additionally comprise other components or ingredients, including non-crystalline fusidic acid or derivatives of fusidic acid.

Crystalline fusidic acid characterised by exhibiting one or both of the features t) or u), v) or w), respectively, or crystalline fusidic acid hemihydrate may be prepared according to methods disclosed in Patent ES 2208110, which is hereby incorporated by reference.

In yet another more specific aspect, this invention relates to a mixture of crystalline forms of fusidic acid, which comprises 70-99.99 (mol %), e.g. 90-99.9 (mol) %, such as 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.5, 99.6, 99.7, 99.8, or 99.9 (mol %), of crystalline fusidic acid hemihydrate, further comprising 0.01-30 (mol %), e.g. 0.1-10 (mol %), such as 0.1, 0.2, 0.3, 0.4, 0.5, 1, 2, 3, 4, 5, 6, 7, 8, 9, 10, 11, 12, 13, 14, 15, 16, 17, 18, 19, 20, 21, 23, 24, 25, 26, 27, 28, 29, or 30 (mol %), of crystalline fusidic acid of the present invention as described above.

In yet another a more specific aspect, this invention relates to a polymorph of fusidic acid which is characterised by exhibiting an angle of reflection (2θ) at approximately 22.7 (±0.1) exceeding 30% with respect to the largest intensity peak in an X-ray powder diffractogram (XRD) the absence of angles of reflection (2θ) in an X-ray powder diffractogram (XRD) in the range of 10.2-12.0 (±0.1) exceeding 5% with respect to the largest intensity peak, and/or which is characterised by the absence of an intensity peak at 1743 (±1 $cm^{-1}$) exceeding 10% with respect to the largest intensity peak in a fourier transform (FT-NIR) Raman spectrum.

The crystalline fusidic acid of the present invention is useful for treating, preventing or ameliorating infections in a patient, including a mammalian, and in particular, a human patient. Animals that may be treated with a compound of the invention include, more specifically, domestic animals such as horses, cows, pigs, sheep, poultry, fish, cats, dogs and zoo animals. The crystalline fusidic acid of the present invention may be particularly useful in the treatment of bacterial infections, such as skin infections or secondary skin infections, or eye infections. The crystalline fusidic acid of the present invention may be furthermore useful in the treatment of simple abscesses, impetiginous lesions, furuncles, or cellulites. The crystalline fusidic acid of the present invention may be particularly useful for the treatment, e.g. the topical treatment, of contagious superficial infections of the skin, such as non-bullous impetigo (or impetigo contagiosa) or bullous impetigo. Consequently, the present invention provides a method of treating, preventing or ameliorating bacterial infections, the method comprising administering to a patient an effective amount of the crystalline fusidic acid, optionally together with another therapeutically active compound. Examples of said other therapeutically active compounds include antibiotics, such as β-lactams, such as penicillins (phenoxymethyl penicillin, benzyl penicillin, dicloxacillin, ampicillin, amoxicillin, pivampicillin, flucloxacillin, piperacillin and mecellinam), cefalosporins (cefalexin, cefalotin, cefepim, cefotaxim, ceftazidim, ceftriazon and cefuroxim), monobactams (aztreonam) and carbapenems (meropenem); macrolides (azithromycin, clarithromycin, erythromycin and roxithromycin); polymyxins (colistin); tetracyclins (tetracycline, doxycyclin, oxytetracyclin and lymecyclin); aminoglycosides (streptomycin, gentamicin, tobramycin and netilmicin); fluoroquinolones (norfloxacin, ofloxacin, ciprofioxacin and moxifloxacin); clindamycin, llncomycin, teicoplanin, vancomycin, oxazolidones (linezolid), rifamycin, metronidazol and fusidic acid. Other compounds which may advantageously be combined with a compound of the invention, especially for topical treatment, include for instance corticosteroids, such as hydrocortisone, betamethasone-17-valerate and triamcinolone acetonid. The crystalline fusidic acid and the other compounds may either be administered concomitantly or sequentially.

The crystalline fusidic acid of the present invention are further useful for the prevention or prophylaxis of bacterial infections in animals and are therefore useful during the breeding of domestic animals, such as mammals, such as horses, cows, pigs, sheep, poultry, fish, cats, dogs and zoo animals.

For use in therapy, the crystalline fusidic acid of the present invention is typically in the form of a pharmaceutical composition. The invention-therefore relates to a pharmaceutical composition comprising crystalline fusidic acid described herein, optionally together with other therapeutically active compounds, together with a pharmaceutically acceptable excipient or vehicle. The excipient must be "acceptable" in the sense of being compatible with the other ingredients of the composition and not deleterious to the recipient thereof. Conveniently, the active ingredient comprises from 0.05-99.9% by weight of the formulation. The formulations include e.g. those in a form suitable for oral (including sustained or timed release), rectal, parenteral (including subcutaneous, intraperitoneal, intramuscular, intraarticular and intravenous), transdermal, ophthalmic, topical, nasal or buccal administration. The formulations may conveniently be presented in dosage unit form and may be prepared by any of the methods well known in the art of pharmacy, e.g. as disclosed in Remington, *The Science and Practlce of Pharmacy*, 20$^{th}$ ed., 2000. All methods include the step of bringing the active ingredient into association with the carrier, which constitutes one or more accessory ingredients. In general, the formulations are prepared by uniformly and intimately bringing the active ingredient into association with a liquid carrier or a finely divided solid carrier or both, and then, if necessary, shaping the product into the desired formulation. Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid, such as ethanol or glycerol; or in the form of an oil-in-water emulsion or a water-in-oil emulsion. Such oils may be edible oils, such as e.g. cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose, hydroxypropylmethylcellulose, hydroxypropylcellulose, carbomers and polyvinylpyrrolidone. The active ingredients may also be administered in the form of a bolus, electuary or paste. A tablet may be made by compressing or moulding the active ingredient optionally with one or more accessory ingredients. Compressed tablets may be prepared by compressing, in a suitable machine, the active ingredient(s) in a free-flowing form such as a powder or granules, optionally mixed by a binder, such as e.g. lactose, glucose, starch, gelatine, acacia gum, tragacanth gum, sodium alginate, carboxymethylcellulose, methylcellulose, hydroxypropylmethylcellulose, polyethylene glycol, waxes or the like; a lubricant such as e.g. sodium oleate, sodium stearate, magnesium stearate, sodium benzoate, sodium acetate, sodium chloride or the like; a disintegrating agent such as e.g. starch, methylcellulose, agar, bentonite, croscarmellose sodium, sodium starch glycollate, crospovidone or the like or a dispersing agent, such as polysorbate 80. Moulded tablets may be made by moulding, in a suitable machine, a mixture of the powdered active ingredient and suitable carrier moistened with an inert liquid diluent. Formulations for rectal administration may be in the form of suppositories in which the compound of the present invention is admixed with low melting water soluble or insoluble solids such as cocoa butter, hydrogenated vegetable oils, polyethylene glycol or fatty acids esters of polyethylene glycols, while elixirs may be prepared using myristyl palmitate. Formulations suitable for parenteral administration conveniently comprise a sterile oily or aqueous preparation of the active ingredients, which is preferably isotonic with the blood of the recipient, e.g. Isotonic saline, isotonic glucose solution or buffer solution. The formulation may be conveniently sterilised by for instance filtration through a bacteria retaining filter, addition of sterilizing agent to the formulation, irradiation of the formulation or heating of the formulation. Liposomal formulations as disclosed in e.g. Encyclopedia of Pharmaceutical Technology, vol. 9, 1994, are also suitable for parenteral administration. Alternatively, the crystalline fusidic acid hemihydrate may be presented as a sterile, solid preparation, e.g. a freeze-dried powder, which is readily dissolved in a sterile solvent immediately prior to use. Transdermal formulations may be in the form of a plaster or a patch. Formulations suitable ophthalmic administration may be in the form of a sterile aqueous preparation of the active ingredients, which may be in microcrystalline form, for example, in the form of an aqueous microcrystalline suspension. Liposomal formulations or biodegradable polymer systems e.g. as disclosed in Encyclopedia of Pharmaceutical Technology, vol. 2, 1989, may also be used to present the active ingredient for ophthalmic administration. Formulations suitable for topical or ophthalmic administration include liquid or semi-liquid preparations such as liniments, lotions, gels, applicants, oil-in-water or water-in-oil emulsions such as creams, ointments or pastes; or solutions or suspensions such as drops. Formulations suitable for nasal or buccal administration include powder, self-propelling and spray formulations, such as aerosols and atomisers. Such formulations are disclosed in greater detail in e.g. *Modern Pharmaceutics*, 2$^{nd}$ ed., G. S. Banker and C. T. Rhodes (Eds.), page 427-432, Marcel Dekker, New York; *Modern Pharmaceutics*, 3$^{th}$ ed., G. S. Banker and C. T. Rhodes (Eds.), page 618-619 and 718-721, Marcel Dekker, New York and *Encyclopedia of Pharmaceutical Technology* vol. 10. J Swarbrick and J. C. Boylan (Eds), page 191-221, Marcel Dekker, New York. In addition to the aforementioned ingredients, the formulations of a compound of crystalline fusidic acid hemihydrate may include one or more additional ingredients such as diluents, buffers, flavouring agents, colourant, surface active agents, thickeners, preservatives, e.g. methyl hydroxybenzoate (including anti-oxidants), emulsifying agents and the like.

The parenteral formulations are in particular useful in the treatment of conditions in which a quick response to the treatment is desirable. In the continuous therapy of patients suffering from infectious diseases, the tablets or capsules may be the appropriate form of pharmaceutical preparation owing to the prolonged effect obtained when the drug is given orally, in particular in the form of sustained-release tablets. As suggested above, the composition may contain other therapeutically active components, which can appropriately be administered together with the compounds of the invention in the treatment of infectious diseases, such as other suitable antibiotics, in particular such antibiotics which may enhance the activity and/or prevent development of resistance. Corticosteroids may also beneficially be included in the compositions of the present invention. In particular, said other active component may include β-lactams, such as penicillins (phenoxymethyl penicillin, benzyl penicillin, dicloxacillin, ampicillin, amoxicillin, pivampicillin, flucloxacillin, piperacillin and mecellinam), cefalosporins (cefalexin, cefalotin, cefepim, cefotaxim, ceftazidim, ceftriazon and cefuroxim), monobactams (aztreonam) and carbapenems (meropenem); macrolides (azithromycin, clarithromycin, erythromycin and roxithromycin); polymyxins (colistin); tetracyclins (tetracycline, doxycyclin, oxytetracyclin and lymecyclin); aminoglycosides (streptomycin, gentamicin, tobramycin and netilmicin); fluoroquinolones (norfloxacin, ofloxacin, ciprofloxacin and moxifloxacin); clindamycin, lincomycin, telcoplanin, vancomycin, oxazolidones (linezolid), rifamycin, metronidazol and fusidic acid. Other compounds which advantageously may be combined with the compounds of the invention, especially for topical treatments, include e.g. corticosteroids, such as hydrocortisone, betamethason-17-valerate and triamcinolone acetonid.

The other therapeutically active compound may be in the same or separate containers adapted for concomitant or sequential administration of said therapeutically active compounds.

The treatment of infectious diseases often involves determining whether said disease is resistant or refractory to the treatment, before the treatment is, in fact, initiated. By way of example, samples containing the infectious microbe may be taken from the patient, e.g. blood or urine, after which the sample is cultured and exposed to the treatment to determine whether said infectious organism responds to the treatment. Accordingly, the present invention also provides a method for identifying compounds effective against a micro organism, the method comprising administering crystalline fusidic acid of the present invention as described above, optionally together with other therapeutically active agents, to a micro organism, and determining whether said compound or mixture of compounds has a toxic or static effect on the micro organism in question.

The compositions of the present invention are not limited to pharmaceuticals, but may also be used in a non-therapeutic context to control microbial growth. For example may compositions or compounds of the present invention be useful as additives which inhibit microbial growth, such as during fermentation processes. By way of example, the selectivity of antimicrobial agents renders them useful to enhance growth of particular micro organisms at the expense of others in a multi-species culture.

In yet another more specific aspect, this invention relates to a pharmaceutical composition comprising crystalline fusidic acid of the present invention as described above together with a pharmaceutically acceptable excipient or vehicle further comprising another therapeutically active compound is selected from the group consisting of antibiotics and corticosteroids.

In yet another more specific aspect, this invention relates to a pharmaceutical composition comprising crystalline fusidic acid of the present invention as described above together with a pharmaceutically acceptable excipient or vehicle further comprising another therapeutically active compound selected from the group consisting of penicillins (phenoxymethyl penicillin, benzyl penicillin, dicloxacillin, ampicillin, amoxicillin, pivampicillin, flucloxacillin, piperacillin and mecellinam), cefalosporins (cefalexin, cefalotin, cefepim, cefotaxim, ceftazidim, ceftriazon and cefuroxim), monobactams (aztreonam) and carbapenems (meropenem); macrolides (azithromycin, clarithromycin, erythromycin and roxithromycin); polymyxins (colistin); tetracyclins (tetracycline, doxycyclin, oxytetracyclin and lymecyclin); aminoglycosides (streptomycin, gentamicin, tobramycin and netilmicin); fluoroquinolones (norfloxacin, ofloxacin, ciprofloxacin and moxifloxacin); clindamycin, lincomycin, teicoplanin, vancomycin, oxazolidones (linezolid), rifamycin, metronidazol, fusidic acid, hydrocortisone, betamethason-17-valerate and triamcinolone acetonid.

In yet another more specific aspect, this invention relates to a method of treating, preventing or ameliorating infections in a patient, the method comprising administering to said patient an effective amount of crystalline fusidic acid of the present invention as described above, and optionally further comprising concomitant or sequential administration of one or more other therapeutically active compounds, wherein said other therapeutically active compound is selected from the group consisting of antibiotics and corticosteroids.

In yet another more specific aspect, this invention relates to a method of treating, preventing or ameliorating infections in a patient, such as a bacterial infection the method comprising administering to said patient an effective amount of crystalline fusidic acid of the present invention as described above, and optionally further comprising concomitant or sequential administration of one or more other therapeutically active compounds, wherein said other therapeutically active compound is selected from the group consisting of penicillins (phenoxymethyl penicillin, benzyl penicillin, dicloxacillin, ampicillin, amoxicillin, pivampicillin, flucloxacillin, piperacillin and mecellinam), cefalosporins. (cefalexin, cefalotin, cefepim, cefotaxim, ceftazidim, ceftriazon and cefuroxim), monobactams (aztreonam) and carbapenems (meropenem); macrolides (azithromycin, clarithromycin, erythromycin and roxithromycin); polymyxins (colistin); tetracyclins (tetracycline, doxycyclin, oxytetracyclin and lymecyclin); aminoglycosides (streptomycin, gentamicin, tobramycin and netilmicin); fluoroquinolones (norfloxacin, ofloxacin, ciprofloxacin and moxifloxacin); clindamycin, lincomycin, teicoplanin, vancomycin, oxazolidones (linezolid), rifamycin, metronidazol, fusidic acid, hydrocortisone, betamethason-17-yalerate and triamcinolone acetonid.

In yet another more specific aspect, this invention relates to the use of crystalline fusidic acid of the present invention as described above for the manufacture of a medicament for the treatment, amelioration or prophylaxis of infections, such as a bacterial infection, wherein said medicament further comprises another therapeutically active compound in the same or separate containers adapted for concomitant or sequential administration of said therapeutically active compounds.

In yet another more specific aspect, this invention relates to the use of crystalline fusidic acid of the present invention as described above for the manufacture of a medicament for the treatment, amelioration or prophylaxis of infections, such as a bacterial infection, wherein said medicament further comprises another therapeutically active compound in the same or separate containers adapted for concomitant or sequential administration of said therapeutically active compounds, wherein said other therapeutically active compound is selected from the group consisting of penicillins (phenoxymethyl penicillin, benzyl penicillin, dicloxacillin, ampicillin, amoxicillin, pivampicillin, flucloxacillin, piperacillin and mecellinam), cefalosporins (cefalexin, cefalotin, cefepim, cefotaxim, ceftazidim, ceftriaxon and cefuroxim), monobactams (aztreonam) and carbapenems (meropenem); macrolides (azithromycin, clarithromycin, erythromycin and roxithromycin); polymyxins (colistin); tetracyclins (tetracycline, doxycyclin, oxytetracyclin and lymecyclin); aminoglycosides (streptomycin, gentamicin, tobramycin and netilmicin); fluoroquinolones (norfloxacin, ofloxacin, ciprofloxacin and moxifloxacin); clindamycin, lincomycin, telcoplanin, vancomycin, oxazolidones (linezolid), rifamycin, metronidazol, fusidic acid, hydrocortisone, betamethason-17-valerate and trlamcinolone acetonid.

The fusidic acid of the present invention may have advantageous storage stability in comparison to known polymorphic forms. Production batches of crude fusidic acid may therefore be transformed to the crystal form of the present invention in order to limit degradation during storage. Then, e.g. shortly prior to manufacture of the presently preferred pharmaceutical formulations which comprise fusidic acid hemihydrate, the more stable anhydrous and solvent free form of fusidic acid of the present invention may then be advantageously be transformed to the presently marketed hemihydrate form. The methods disclosed in this application for the transformation or synthesis of the fusidic acid of the present invention, including the methods described in the examples, may use any polymorphic form of fusidic acid as a starting material.

In yet another more specific aspect this invention relates to a method for the preparation of crystalline fusidic acid of the present invention as described above, said method comprising the steps of a) dissolving or suspending fusidic acid hemihydrate in a solvent which is capable of dissolving said fusidic acid hemihydrate and in which the crystalline fusidic acid of the present invention is essentially insoluble or sparingly soluble, such as a water miscible organic solvent, optionally with heating, to give a suspension or solution;

b) optionally heating said suspension or solution, or keeping said suspension or solution at the elevated temperature after heating in step a);

c) optionally cooling or concentrating said suspension or solution;

d) isolating the crystalline fusidic acid of the present invention.

In yet another embodiment, the solvent used in the preparation method of the crystalline fusidic acid of the present invention in step a) above is an alkylester of formic acid, such as ethylformate, a $C_1$-$C_4$ alcohol, such as ethanol, $C_1$-$C_4$ alkylacetate, acetonitrile, acetone, or mixtures thereof, or mixtures of said solvents with water, most preferably a mixture of ethanol and water, e.g. 50:50 (v:v), or a mixture of methanol and water, e.g. 50:50 (v:v).

In yet another embodiment, the solvent used in the preparation method of the crystalline fusidic acid of the present invention in step a) above is heated to about 50° C. during the step of dissolving the fusidic acid hemihydrate.

In yet another embodiment the suspension or solution is kept at about 50° C. for 3-4 hours in step b) above before cooling and isolation of the crystalline fusidic acid.

In yet another embodiment the suspension or solution is cooled to about 0-10° C. In step c) above before isolation of the crystalline fusidic acid.

In yet another embodiment the fusidic acid hemihydrate is completely dissolved with heating in step a) above until a clear solution is obtained; optionally keeping said suspension or solution at the elevated temperature after heating in step a); followed by cooling in step c) above until crystalline fusidic acid of the present invention as described above precipitates.

In yet another more specific aspect this invention relates to a method for the preparation of crystalline fusidic acid of the present invention as described above, said method comprising the steps of e) dissolving fusidic acid in acetonitrile, acrylonitrile, adiponitrile, benzonitrile, propanenitrile, or mixtures of said solvents with heating;

f) cooling of the solution obtained in e) to 5-30° C., such as to 20-25° C.;

g) allowing crystalline fusidic acid according of the present invention as described above to crystallise;

h) isolating the crystalline fusidic acid of the present invention as described above.

In yet another more specific aspect, this invention relates to a method for the preparation of crystalline fusidic acid of the present invention as described above, said method comprising the steps of j) mixing fusidic acid with water, ethanol, a mixture of methanol and water, acetonitrile, ethyl formate, or mixtures of said solvents;

k) stirring of the mixture obtained in step j), optionally with heating followed by cooling, until a suspension is obtained in which the suspended crystals essentially consist of crystalline fusidic of the present invention as described above;

l) isolating the crystalline fusidic acid of the present invention as described above from the suspension.

Definitions

The term "polymorphic purity" includes the purity relative to other polymorphic and pseudopolymorphic crystal forms.

The term "$C_1$-$C_4$ alcohol" includes methanol, ethanol, 1-propanol, 2-propanol, 1-butanol, tert-butanol, and 2-butanol.

The term "$C_1$-$C_4$ alkylacetate" includes ethylacetate, tert-butylacetate, isopropylacetate, n-propylacetate, 2-butylacetate, 1-butylacetate, methylacetate.

The term "ethanol" in the context of the present invention includes but is not limited to all commercially available grades of ethanol, such as anhydrous ethanol or ethanol from obtained from azeotropic distillation containing water, typically containing 4-5% water, commonly named alcohol.

The term "polymorph" encompasses all solid forms, e.g. amorphous solids or solid crystal forms, including solvates with stoichiometric or non-stochiometric amounts of solvent and hydrates with stochiometric or non stoichiometric amounds of water.

The term "crystalline forms" encompasses crystalline polymorphs in all degrees of crystallinity.

Experimental

Analytical Methods

X-ray powder diffraction: The diffractogram was obtained in the range 3-30 degrees 2 Theta on a STADI-P instrument from STOE&CIE GmbH. [Diffractometer: transmission; monochromator: curved germanium (111); wavelength: 1.540598 Cu; detector: linear PSD; scan mode: transmission/moving PSD/fixed omega; scan type: 2theta:omega] FTIR spectroscopy (attenuated total reflectance fourier transform infrared spectroscopy): The spectrum was recorded on a FTIR instrument equipped with a GoldenGate ATR unit from SPECAC.

FT-IR may be performed on KBr pellets in a NICOLET Avatar 360 FT-IR equipment. Raman spectroscopy: The spectrum was recorded on a FTNIR-Raman instrument, RFS 100/S from Bruker.

NIR reflection spectroscopy: The spectrum was recorded using a fiber optic probe coupled to a FTIR instrument, Equinox 55 from Bruker.

The $^{13}$C CP/MAS (Cross-polarization/Magic Angle Spinning) solid-state nuclear magnetic resonance (NMR) spectrum (micronised sample) was acquired with Varian Unity-INOVA NMR spectrometer with a magnetic field strength of 7.04 T operating at 75.42 MHz for $^{13}$C. A 5 mm homebuilt CP/MAS TLT (Transmission Line Tuning) probe using a spinning frequency of 5.0 kHz was used. The $^{13}$C spectrum was obtained using a standard cross-polarization pulse sequence using a contact time of 1.2 ms, a relaxation delay of 4 sec, a dwell time of 10 µsec, spectral width of 50 kHz, and at ambient temperature. Proton decoupling was performed using a decoupling field strength of 110 kHz. The 5 mm $Si_3N_4$ rotor has a sample volume of 110 µl and contained 103 mg substance. The total acquisition time was 21.5 hours.

The spectrum was processed with zerofilling (32K real points), exponential multiplication and line broadening of 30 Hz. The spectrum was referenced to an external of TMS. Chemical shifts given in ppm relative to an external reference of TMS The given error ranges in this application for the spectroscopic characteristics, including those in the claims, may be more or less depending of factors well known to a person skilled in the art of spectroscopy and may for example depend on sample preparation, such as particle size distribution, or if the crystal form is part of a formulation, on the composition of the formulation, as well as instrumental fluctuations, and other factors. An error range of ±5 includes, but is not limited to variations of ±5, ±4, ±3, ±2, ±1, ±0.5, ±0.5, ±0.4, ±0.3, ±0.2, and ±0.1; an error range of ±3 includes, but is not limited to variations of ±3, ±2, ±1, ±0.5, ±0.5, ±0.4, ±0.3, ±0.2, and ±0.1; an error range of ±1 includes, but is not limited to variations of ±0.9, ±0.8, ±0.7, ±0.6, ±0.5, ±0.4, ±0.3, ±0.2, and ±0.1; and an error range of ±0.2 includes, but is not limited to variations of ±0.2, ±0.15, ±0.1, ±0.09, ±0.08, ±0.07, ±0.06, ±0.05, ±0.04, ±0.03, ±0.02, and ±0.01.

Single crystal X-ray diffraction: Single crystal data were obtained on a Siemens SMART CCD Platform (experimental details and detailed results se below):

audit_creation_method: SHELXL-97; chemical_formula_sum 'C31 H48 O6';
chemical_formula_weight 516.69;
_atom_type_symbol
_atom_type_description
_atom_type_scat_dispersion_real
_atom_type_scat_dispersion_imag
_atom_type_scat_source
 'C' 'C' 0.0033  0.0016

'International Tables Vol C Tables 4.2.6.8 and 6.1.1.4'
 'H' 'H' 0.0000  0.0000
'International Tables Vol C Tables 4.2.6.8 and 6.1.1.4'
 'O' 'O' 0.0106  0.0060
'International Tables Vol C Tables 4.2.6.8 and 6.1.1.4'
_symmetry_cell_setting              monoclinic
_symmetry_space_group_name_H-M      'P 21'
_symmetry_equiv_pos_as_xyz
 'x, y, z'
 '-x, y + ½, -z'
_cell_length_a                      12.2259(12)
_cell_length_b                      8.0201(8)
_cell_length_c                      13.9120(13)
_cell_angle_alpha                   90.00
_cell_angle_beta                    94.267(2)
_cell_angle_gamma                   90.00
_cell_volume                        1360.3(2)
_cell_formula_units_Z               2
_cell_measurement_temperature       120(2)
_exptl_crystal_colour               colourless
_exptl_crystal_size_max             0.30
_exptl_crystal_size_mid             0.13
_exptl_crystal_size_min             0.08
_exptl_crystal_density_diffrn       1.261
_exptl_crystal_density_method       'not measured'
_exptl_crystal_F_000                564
_exptl_absorpt_coefficient_mu       0.085
_exptl_absorpt_correction_type      multi-scan
_exptl_absorpt_correction_T_min     0.8360
_exptl_absorpt_correction_T_max     1.0000
_exptl_absorpt_process_details      'SADABS, ver2.03 (Sheldrick, 2001)'
_diffrn_ambient_temperature         120(2)
_diffrn_radiation_wavelength        0.71073
_diffrn_radiation_type              MoK\a
_diffrn_radiation_source            'normal-focus sealed tube'
_diffrn_radiation_monochromator     graphite
_diffrn_measurement_device_type     'Siemens SMART CCD Platform'
_diffrn_measurement_method          'omega scans'
_diffrn_standards_number            no
_diffrn_standards_interval_count    no
_diffrn_standards_interval_time     no
_diffrn_standards_decay_%           'no decay'
_diffrn_reflns_number               9700
_diffrn_reflns_av_R_equivalents     0.0225
_diffrn_reflns_av_sigmaI/netI       0.0489
_diffrn_reflns_limit_h_min          -16
_diffrn_reflns_limit_h_max          15
_diffrn_reflns_limit_k_min          -10
_diffrn_reflns_limit_k_max          10
_diffrn_reflns_limit_l_min          -18
_diffrn_reflns_limit_l_max          17
_diffrn_reflns_theta_min            1.47
_diffrn_reflns_theta_max            28.00
_reflns_number_total                6264
_reflns_number_gt                   5748
_reflns_threshold_expression        >2sigma(I)
_computing_data_collection          'SMART (Bruker AXS, 1998)'
_computing_cell_refinement          'SAINT (Bruker AXS, 1998)'
_computing_data_reduction           'SAINT (Bruker AXS, 1998)'
_computing_structure_solution       'SHELXTL, ver.6.12 (Sheldrick, 2001)'
_computing_structure_refinement     'SHELXTL, ver.6.12 (Sheldrick, 2001)'
_computing_molecular_graphics       'SHELXTL, ver.6.12 (Sheldrick, 2001)'
_refine_special_details;

Refinement of $F^2$ against ALL reflections. The weighted R-factor wR and goodness of fit S are based on $F^2$, conventional R-factors R are based on F, with F set to zero for negative $F^2$. The threshold expression of $F^2 > 2\text{sigma}(F^2)$ is used only for calculating R-factors(gt) etc. and is not relevant to the choice of reflections for refinement. R-factors based on $F^2$ are statistically about twice as large as those based on F, and R-factors based on ALL data will be even larger.

```
_refine_ls_structure_factor_coef      Fsqd
_refine_ls_matrix_type                full
_refine_ls_weighting_scheme           calc
_refine_ls_weighting_details
 'calc w = 1/[\s^2^(Fo^2^) + (0.0623P)^2^ + 0.0598P] where P = (Fo^2^+ 2Fc^2^)/3'
_atom_sites_solution_primary          direct
_atom_sites_solution_secondary        difmap
_atom_sites_solution_hydrogens        geom
_refine_ls_hydrogen_treatment         mixed
_refine_ls_extinction_method          none
_refine_ls_abs_structure_details
 'Flack H D (1983), Acta Cryst. A39, 876-881, 2986 Friedel pairs'
_refine_ls_abs_structure_Flack        −0.3(8)
_refine_ls_number_reflns              6264
_refine_ls_number_parameters          334
_refine_ls_number_restraints          1
_refine_ls_R_factor_all               0.0544
_refine_ls_R_factor_gt                0.0492
_refine_ls_wR_factor_ref              0.1156
_refine_ls_wR_factor_gt               0.1127
_refine_ls_goodness_of_fit_ref        1.080
_refine_ls_restrained_S_all           1.080
_refine_ls_shift/su_max               0.001
_refine_ls_shift/su_mean              0.000
_atom_site_label
_atom_site_type_symbol
_atom_site_fract_x
_atom_site_fract_y
_atom_site_fract_z
_atom_site_U_iso_or_equiv
_atom_site_adp_type
_atom_site_occupancy
_atom_site_symmetry_multiplicity
_atom_site_calc_flag
_atom_site_refinement_flags
_atom_site_disorder_assembly
_atom_site_disorder_group
```

| Label | Type | x | y | z | U | ADP | Misc |
|---|---|---|---|---|---|---|---|
| O1   | O | 0.65498(11) | 0.7043(2)   | 0.22466(11) | 0.0221(3) | Uani | 1 1 d ... |
| H10  | H | 0.6856      | 0.7577      | 0.1822      | 0.027     | Uiso | 1 1 calc R ... |
| C1   | C | 0.73560(16) | 0.6031(2)   | 0.27926(14) | 0.0160(4) | Uani | 1 1 d ... |
| H1   | H | 0.6985      | 0.4973      | 0.2966      | 0.019     | Uiso | 1 1 calc R ... |
| C2   | C | 0.76897(16) | 0.6944(3)   | 0.37299(14) | 0.0184(4) | Uani | 1 1 d ... |
| H21  | H | 0.8048      | 0.6146      | 0.4196      | 0.022     | Uiso | 1 1 calc R ... |
| H22  | H | 0.7024      | 0.7376      | 0.4009      | 0.022     | Uiso | 1 1 calc R ... |
| C3   | C | 0.84748(15) | 0.8396(3)   | 0.35837(14) | 0.0159(4) | Uani | 1 1 d ... |
| H31  | H | 0.8711      | 0.8887      | 0.4218      | 0.019     | Uiso | 1 1 calc R ... |
| H32  | H | 0.8081      | 0.9271      | 0.3193      | 0.019     | Uiso | 1 1 calc R ... |
| C4   | C | 0.94949(15) | 0.7849(2)   | 0.30780(13) | 0.0123(4) | Uani | 1 1 d ... |
| C5   | C | 1.01283(15) | 0.6539(2)   | 0.37206(14) | 0.0150(4) | Uani | 1 1 d ... |
| H51  | H | 1.0404      | 0.7060      | 0.4328      | 0.018     | Uiso | 1 1 calc R ... |
| H52  | H | 1.0746      | 0.6109      | 0.3385      | 0.018     | Uiso | 1 1 calc R ... |
| H53  | H | 0.9635      | 0.5618      | 0.3855      | 0.018     | Uiso | 1 1 calc R ... |
| C6   | C | 0.90700(15) | 0.7088(2)   | 0.20892(13) | 0.0121(4) | Uani | 1 1 d ... |
| H6   | H | 0.8594      | 0.7957      | 0.1756      | 0.015     | Uiso | 1 1 calc R ... |
| C7   | C | 0.83272(15) | 0.5557(2)   | 0.22159(13) | 0.0140(4) | Uani | 1 1 d ... |
| H7   | H | 0.8771      | 0.4707      | 0.2599      | 0.017     | Uiso | 1 1 calc R ... |
| C8   | C | 0.79120(16) | 0.4742(3)   | 0.12612(14) | 0.0165(4) | Uani | 1 1 d ... |
| H81  | H | 0.7526      | 0.5574      | 0.0847      | 0.020     | Uiso | 1 1 calc R ... |
| H82  | H | 0.7409      | 0.3830      | 0.1389      | 0.020     | Uiso | 1 1 calc R ... |
| H83  | H | 0.8536      | 0.4300      | 0.0938      | 0.020     | Uiso | 1 1 calc R ... |
| C9   | C | 1.03627(15) | 0.9273(2)   | 0.29252(13) | 0.0121(4) | Uani | 1 1 d ... |
| H9   | H | 1.1080      | 0.8677      | 0.3028      | 0.015     | Uiso | 1 1 calc R ... |
| C10  | C | 1.03978(15) | 0.9997(2)   | 0.18856(13) | 0.0115(4) | Uani | 1 1 d ... |
| C11  | C | 0.93605(15) | 1.1020(2)   | 0.15689(15) | 0.0159(4) | Uani | 1 1 d ... |
| H111 | H | 0.9339      | 1.1230      | 0.0874      | 0.019     | Uiso | 1 1 calc R ... |
| H112 | H | 0.9379      | 1.2085      | 0.1915      | 0.019     | Uiso | 1 1 calc R ... |
| H113 | H | 0.8706      | 1.0394      | 0.1717      | 0.019     | Uiso | 1 1 calc R ... |
| C12  | C | 1.04989(17) | 0.8530(3)   | 0.11609(14) | 0.0167(4) | Uani | 1 1 d ... |
| H121 | H | 1.0113      | 0.8850      | 0.0538      | 0.020     | Uiso | 1 1 calc R ... |
| H122 | H | 1.1284      | 0.8383      | 0.1050      | 0.020     | Uiso | 1 1 calc R ... |
| C13  | C | 1.00412(15) | 0.6838(2)   | 0.14719(13) | 0.0141(4) | Uani | 1 1 d ... |
| H131 | H | 0.9803      | 0.6178      | 0.0893      | 0.017     | Uiso | 1 1 calc R ... |
| H132 | H | 1.0626      | 0.6208      | 0.1844      | 0.017     | Uiso | 1 1 calc R ... |
| C14  | C | 1.04371(15) | 1.0609(3)   | 0.37220(14) | 0.0152(4) | Uani | 1 1 d ... |
| H14  | H | 1.0486      | 1.0030      | 0.4360      | 0.018     | Uiso | 1 1 calc R ... |
| O2   | O | 0.95324(11) | 1.17668(18) | 0.37013(10) | 0.0198(3) | Uani | 1 1 d ... |
| H2   | H | 0.8944      | 1.1259      | 0.3548      | 0.024     | Uiso | 1 1 calc R ... |
| C15  | C | 1.14475(15) | 1.1727(3)   | 0.36786(13) | 0.0160(4) | Uani | 1 1 d ... |
| H151 | H | 1.1437      | 1.2611      | 0.4174      | 0.019     | Uiso | 1 1 calc R ... |
| H152 | H | 1.2122      | 1.1057      | 0.3810      | 0.019     | Uiso | 1 1 calc R ... |
| C16  | C | 1.14421(15) | 1.2510(2)   | 0.26831(14) | 0.0124(4) | Uani | 1 1 d ... |

-continued

| | | | | | | |
|---|---|---|---|---|---|---|
| H16 | H | 1.0726 | 1.3108 | 0.2575 | 0.015 | Uiso 1 1 calc R . . . |
| C17 | C | 1.14461(15) | 1.1141(2) | 0.18902(13) | 0.0120(4) | Uani 1 1 d . . . |
| C18 | C | 1.25268(15) | 1.0140(2) | 0.20317(15) | 0.0158(4) | Uani 1 1 d . . . |
| H181 | H | 1.2711 | 0.9680 | 0.1411 | 0.019 | Uiso 1 1 calc R . . . |
| H182 | H | 1.2436 | 0.9228 | 0.2488 | 0.019 | Uiso 1 1 calc R . . . |
| H183 | H | 1.3119 | 1.0878 | 0.2286 | 0.019 | Uiso 1 1 calc R . . . |
| C19 | C | 1.15151(15) | 1.2236(2) | 0.09921(14) | 0.0150(4) | Uani 1 1 d . . . |
| H191 | H | 1.1768 | 1.1577 | 0.0449 | 0.018 | Uiso 1 1 calc R . . . |
| H192 | H | 1.0791 | 1.2729 | 0.0793 | 0.018 | Uiso 1 1 calc R . . . |
| C20 | C | 1.23484(15) | 1.3599(3) | 0.13003(13) | 0.0139(4) | Uani 1 1 d . . . |
| H20 | H | 1.2132 | 1.4685 | 0.0989 | 0.017 | Uiso 1 1 calc R . . . |
| O3 | O | 1.34681(11) | 1.31568(17) | 0.11003(9) | 0.0153(3) | Uani 1 1 d . . . |
| C21 | C | 1.23201(15) | 1.3722(2) | 0.23942(13) | 0.0128(4) | Uani 1 1 d . . . |
| C22 | C | 1.37481(17) | 1.3391(3) | 0.01975(15) | 0.0190(4) | Uani 1 1 d . . . |
| O4 | O | 1.31116(12) | 1.3796(2) | −0.04657(11) | 0.0249(4) | Uani 1 1 d . . . |
| C23 | C | 1.49545(19) | 1.3081(3) | 0.01339(17) | 0.0292(5) | Uani 1 1 d . . . |
| H231 | H | 1.5113 | 1.2996 | −0.0545 | 0.035 | Uiso 1 1 calc R . . . |
| H232 | H | 1.5162 | 1.2039 | 0.0467 | 0.035 | Uiso 1 1 calc R . . . |
| H233 | H | 1.5374 | 1.4007 | 0.0438 | 0.035 | Uiso 1 1 calc R . . . |
| C24 | C | 1.29903(15) | 1.4747(2) | 0.29277(14) | 0.0143(4) | Uani 1 1 d . . . |
| C25 | C | 1.38157(15) | 1.5748(2) | 0.24192(14) | 0.0151(4) | Uani 1 1 d . . . |
| O5 | O | 1.36242(11) | 1.65776(18) | 0.17072(10) | 0.0196(3) | Uani 1 1 d . . . |
| O6 | O | 1.48109(11) | 1.5626(2) | 0.28729(11) | 0.0233(3) | Uani 1 1 d . . . |
| H60 | H | 1.5253 | 1.6220 | 0.2590 | 0.028 | Uiso 1 1 calc R . . . |
| C26 | C | 1.30545(16) | 1.4964(3) | 0.40155(14) | 0.0165(4) | Uani 1 1 d . . . |
| H261 | H | 1.3668 | 1.4276 | 0.4302 | 0.020 | Uiso 1 1 calc R . . . |
| H262 | H | 1.2369 | 1.4530 | 0.4259 | 0.020 | Uiso 1 1 calc R . . . |
| C27 | C | 1.32209(17) | 1.6762(3) | 0.43647(14) | 0.0188(4) | Uani 1 1 d . . . |
| H271 | H | 1.3933 | 1.7180 | 0.4168 | 0.023 | Uiso 1 1 calc R . . . |
| H272 | H | 1.2634 | 1.7474 | 0.4055 | 0.023 | Uiso 1 1 calc R . . . |
| C28 | C | 1.32032(16) | 1.6892(3) | 0.54453(14) | 0.0177(4) | Uani 1 1 d . . . |
| H28 | H | 1.2554 | 1.7315 | 0.5691 | 0.021 | Uiso 1 1 calc R . . . |
| C29 | C | 1.40217(18) | 1.6463(3) | 0.60835(15) | 0.0230(5) | Uani 1 1 d . . . |
| C30 | C | 1.3906(2) | 1.6556(3) | 0.71529(16) | 0.0352(6) | Uani 1 1 d . . . |
| H301 | H | 1.3153 | 1.6873 | 0.7269 | 0.042 | Uiso 1 1 calc R . . . |
| H302 | H | 1.4416 | 1.7391 | 0.7441 | 0.042 | Uiso 1 1 calc R . . . |
| H303 | H | 1.4074 | 1.5465 | 0.7445 | 0.042 | Uiso 1 1 calc R . . . |
| C31 | C | 1.5114(2) | 1.5869(4) | 0.5808(2) | 0.0409(7) | Uani 1 1 d . . . |
| H311 | H | 1.5198 | 1.4683 | 0.5966 | 0.049 | Uiso 1 1 calc R . . . |
| H312 | H | 1.5696 | 1.6507 | 0.6163 | 0.049 | Uiso 1 1 calc R . . . |
| H313 | H | 1.5163 | 1.6027 | 0.5114 | 0.049 | Uiso 1 1 calc R . . . |

_atom_site_aniso_label
_atom_site_aniso_U_11
_atom_site_aniso_U_22
_atom_site_aniso_U_33
_atom_site_aniso_U_23
_atom_site_aniso_U_13
_atom_site_aniso_U_12

| | | | | | | |
|---|---|---|---|---|---|---|
| O1 | 0.0118(7) | 0.0289(8) | 0.0259(8) | 0.0100(7) | 0.0035(6) | −0.0005(6) |
| C1 | 0.0137(9) | 0.0170(10) | 0.0172(10) | 0.0023(8) | 0.0007(7) | −0.0036(7) |
| C2 | 0.0156(9) | 0.0222(10) | 0.0184(10) | −0.0012(8) | 0.0069(8) | −0.0034(8) |
| C3 | 0.0156(9) | 0.0178(10) | 0.0150(10) | −0.0014(8) | 0.0052(7) | −0.0026(8) |
| C4 | 0.0123(9) | 0.0145(9) | 0.0100(9) | −0.0005(7) | 0.0010(7) | −0.0013(7) |
| C5 | 0.0142(9) | 0.0157(9) | 0.0150(9) | 0.0020(8) | −0.0002(7) | −0.0020(8) |
| C6 | 0.0119(8) | 0.0124(9) | 0.0120(9) | −0.0008(7) | 0.0002(7) | −0.0004(7) |
| C7 | 0.0139(9) | 0.0144(9) | 0.0135(9) | 0.0010(7) | 0.0012(7) | −0.0029(7) |
| C8 | 0.0178(10) | 0.0157(9) | 0.0159(10) | −0.0005(8) | 0.0002(8) | −0.0034(8) |
| C9 | 0.0106(9) | 0.0132(9) | 0.0128(9) | −0.0011(7) | 0.0022(7) | −0.0007(7) |
| C10 | 0.0112(8) | 0.0121(9) | 0.0112(9) | −0.0002(7) | 0.0006(7) | −0.0023(7) |
| C11 | 0.0130(9) | 0.0161(9) | 0.0182(10) | 0.0033(8) | −0.0018(7) | −0.0030(7) |
| C12 | 0.0211(10) | 0.0170(9) | 0.0126(9) | −0.0020(8) | 0.0050(7) | −0.0080(8) |
| C13 | 0.0131(9) | 0.0150(9) | 0.0142(9) | −0.0007(8) | 0.0015(7) | −0.0010(7) |
| C14 | 0.0153(9) | 0.0188(10) | 0.0118(9) | −0.0012(8) | 0.0032(7) | −0.0052(8) |
| O2 | 0.0175(7) | 0.0192(7) | 0.0236(7) | −0.0070(6) | 0.0070(5) | −0.0038(6) |
| C15 | 0.0169(9) | 0.0185(10) | 0.0125(9) | −0.0005(8) | 0.0016(7) | −0.0053(8) |
| C16 | 0.0108(8) | 0.0130(9) | 0.0134(9) | −0.0008(7) | 0.0003(7) | −0.0024(7) |
| C17 | 0.0116(9) | 0.0129(9) | 0.0113(9) | −0.0002(7) | 0.0007(7) | −0.0004(7) |
| C18 | 0.0133(9) | 0.0156(9) | 0.0189(10) | −0.0007(8) | 0.0034(7) | −0.0005(7) |
| C19 | 0.0156(9) | 0.0173(10) | 0.0120(9) | 0.0000(7) | 0.0007(7) | −0.0040(8) |
| C20 | 0.0119(9) | 0.0169(9) | 0.0132(9) | 0.0004(8) | 0.0033(7) | −0.0010(8) |
| O3 | 0.0137(7) | 0.0186(7) | 0.0140(7) | −0.0009(6) | 0.0044(5) | 0.0002(5) |
| C21 | 0.0114(9) | 0.0160(9) | 0.0112(9) | 0.0013(7) | 0.0035(7) | 0.0025(7) |
| C22 | 0.0198(10) | 0.0194(10) | 0.0184(10) | −0.0054(8) | 0.0051(8) | −0.0062(8) |
| O4 | 0.0230(8) | 0.0363(9) | 0.0162(7) | −0.0021(7) | 0.0055(6) | −0.0056(7) |
| C23 | 0.0197(11) | 0.0427(14) | 0.0265(12) | −0.0048(11) | 0.0112(9) | −0.0013(10) |
| C24 | 0.0123(9) | 0.0148(9) | 0.0157(10) | 0.0009(7) | 0.0005(7) | 0.0015(7) |
| C25 | 0.0152(9) | 0.0139(9) | 0.0165(10) | −0.0050(8) | 0.0039(7) | −0.0015(8) |
| O5 | 0.0198(7) | 0.0171(7) | 0.0223(7) | 0.0035(6) | 0.0032(6) | −0.0032(6) |
| O6 | 0.0121(7) | 0.0329(9) | 0.0252(8) | 0.0079(7) | 0.0018(6) | −0.0049(6) |

-continued

| | | | | | |
|---|---|---|---|---|---|
| C26 | 0.0154(9) | 0.0170(9) | 0.0169(10) | −0.0003(8) | 0.0001(8) | −0.0060(8) |
| C27 | 0.0201(10) | 0.0158(10) | 0.0200(10) | −0.0008(8) | −0.0010(8) | −0.0054(8) |
| C28 | 0.0180(9) | 0.0159(10) | 0.0197(10) | −0.0043(8) | 0.0036(8) | −0.0047(8) |
| C29 | 0.0308(12) | 0.0144(9) | 0.0229(11) | −0.0036(8) | −0.0045(9) | −0.0066(9) |
| C30 | 0.0621(18) | 0.0214(11) | 0.0201(11) | −0.0021(10) | −0.0092(11) | −0.0105(12) |
| C31 | 0.0308(14) | 0.0384(15) | 0.0511(17) | −0.0087(13) | −0.0143(12) | 0.0106(12) |

_geom_special_details;

All esds (except the esd in the dihedral angle between two l.s. planes) are estimated using the full covariance matrix. The cell esds are taken into account individually in the estimation of esds in distances, angles and torsion angles; correlations between esds in cell parameters are only used when they are defined by crystal symmetry. An approximate (isotropic) treatment of cell esds is used for estimating esds involving l.s. planes.;
loop_
_geom_bond_atom_site_label_1
_geom_bond_atom_site_label_2
_geom_bond_distance
_geom_bond_site_symmetry_2
_geom_bond_publ_flag
O1 C1 1.448(2); O1 H10 0.8400; C1 C2 1.524(3); C1 C7 1.530(3); C1 H1 1.0000; C2 C3 1.533(3); C2 H21 0.9900; C2 H22 0.9900; C3 C4 1.541(3); C3 H31 0.9900; C3 H32 0.9900; C4 C5 1.549(3); C4 C6 1.559(3); C4 C9 1.583(3); C5 H51 0.9800; C5 H52 0.9800; C5 H53 0.9800; C6 C13 1.529(3); C6 C7 1.545(3); C6 H6 1.0000; C7 C8 1.533(3); C7 H7 1.0000; C8 H81 0.9800; C8 H82 0.9800; C8 H83 0.9800; C9 C14 1.540(3); C9 C10 1.562(3); C9 H9 1.0000; C10 C11 1.547(3); C10 C12 1.561(3); C10 C17 1.576(3); C11 H111 0.9800; C11 H112 0.9800; C11 H113 0.9800; C12 C13 1.542(3); C12 H121 0.9900; C12 H122 0.9900; C13 H131 0.9900; C13 H132 0.9900; C14 O2 1.443(2); C14 C15 1.531(3); C14 H14 1.0000; O2 H2 0.8400; C15 C16 1.520(3); C15 H151 0.9900; C15 H152 0.9900; C16 C21 1.524(3); C16 C17 1.556(3); C16 H16 1.0000; C17 C19 1.534(3); C17 C18 1.546(3); C18 H181 0.9800; C18 H182 0.9800; C18 H183 0.9800; C19 C20 1.533(3); C19 H191 0.9900; C19 H192 0.9900; C20 O3 1.461(2); C20 C21 1.528(3); C20 H20 1.0000; O3 C22 1.339(2); C21 C24 1.345(3); C22 O4 1.206(2); C22 C23 1.505(3); C23 H231 0.9800; C23 H232 0.9800; C23 H233 0.9800; C24 C25 1.507(3); C24 C26 1.519(3); C25 O5 1.202(2); C25 O6 1.332(2); O6 H60 0.8400; C26 C27 1.531(3); C26 H261 0.9900; C26 H262 0.9900; C27 C28 1.509(3); C27 H271 0.9900; C27 H272 0.9900; C28 C29 1.333(3); C28 H28 0.9500; C29 C31 1.494(3); C29 C30 1.507(3); C30 H301 0.9800; C30 H302 0.9800; C30 H303 0.9800; C31 H311 0.9800; C31 H312 0.9800; C31 H313 0.9800;
_geom_angle_atom_site_label_1
_geom_angle_atom_site_label_2
_geom_angle_atom_site_label_3
_geom_angle
_geom_angle_site_symmetry_1
_geom_angle_site_symmetry_3
_geom_angle_publ_flag
C1 O1 H10 109.5; O1 C1 C2 107.95(16); O1 C1 C7 112.89(16); C2 C1 C7 113.53(15); O1 C1 H1 107.4; C2 C1 H1 107.4; C7 C1 H1 107.4; C1 C2 C3 112.45(16); C1 C2 H21 109.1; C3 C2 H21 109.1; C1 C2 H22 109.1; C3 C2 H22 109.1; H21 C2 H22 107.8; C2 C3 C4 112.36(16); C2 C3 H31 109.1; C4 C3 H31 109.1; C2 C3 H32 109.1; C4 C3 H32 109.1; H31 C3 H32 107.9; C3 C4 C5 108.46(15); C3 C4 C6 106.66(15); C5 C4 C6 111.27(15); C3 C4 C9 115.42(15); C5 C4 C9 104.80(14); C6 C4 C9 110.28(15); C4 C5 H51 109.5; C4 C5 H52 109.5; H51 C5 H52 109.5; C4 C5 H53 109.5; H51 C5 H53 109.5; H52 C5 H53 109.5; C13 C6 C7 116.60(15); C13 C6 C4 108.97(14); C7 C6 C4 111.77(15); C13 C6 H6 106.3; C7 C6 H6 106.3; C4 C6 H6 106.3; C1 C7 C8 109.91(15); C1 C7 C6 110.39(15); C8 C7 C6 113.56(16); C1 C7 H7 107.6; C8 C7 H7 107.6; C6 C7 H7 107.6; C7 C8 H81 109.5; C7 C8 H82 109.5; H81 C8 H82 109.5; C7 C8 H83 109.5; H81 C8 H83 109.5; H82 C8 H83 109.5; C14 C9 C10 113.78(16); C14 C9 C4 114.17(15); C10 C9 C4 117.21(14); C14 C9 H9 103.0; C10 C9 H9 103.0; C4 C9 H9 103.0; C11 C10 C12 108.58(15);; C11 C10 C9 112.50(16); C12 C10 C9 109.06(15); C11 C10 C17 109.98(15); C12 C10 C17 109.76(15); C9 C10 C17 106.93(14); C10 C11 H111 109.5; C10 C11 H112 109.5; H111 C11 H112 109.5; C10 C11 H113 109.5; H111 C11 H113 109.5; H112 C11 H113 109.5; C13 C12 C10 115.75(15); C13 C12 H121 108.3; C10 C12 H121 108.3; C13 C12 H122 108.3; C10 C12 H122 108.3; H121 C12 H122 107.4; C6 C13 C12 110.84(16); C6 C13 H131 109.5; C12 C13 H131 109.5; C6 C13 H132 109.5; C12 C13 H132 109.5; H131 C13 H132 108.1; O2 C14 C15 104.02(16); O2 C14 C9 115.43(15); C15 C14 C9 112.56(16), O2 C14 H14 108.2; C15 C14 H14 108.2; C9 C14 H14 108.2; C14 O2 H2 109.5; C16 C15 C14 109.20(15); C16 C15 H151 109.8; C14 C15 H151 109.8; C16 C15 H152 109.8; C14 C15 H152 109.8; H151 C15 H152 108.3; C15 C16 C21 123.25(16); C15 C16 C17 110.76(15); C21 C16 C17 102.91(15); C15 C16 H16 106.3; C21 C16 H16 106.3; C17 C16 H16 106.3; C19 C17 C18 107.62(16); C19 C17 C16 100.20(15); C18 C17 C16 108.89(15); C19 C17 C10 115.07(14); C18 C17 C10 112.66(15); C16 C17 C10 111.58(15); C17 C18 H181 109.5; C17 C18 H182

-continued

```
109.5; H181 C18 H182 109.5; C17 C18 H183 109.5; H181 C18 H183 109.5; H182
C18 H183 109.5; C20 C19 C17 104.81(15); C20 C19 H191 110.8; C17 C19 H191
110.8; C20 C19 H192 110.8; C17 C19 H192 110.8; H191 C19 H192 108.9; O3 C20
C21 107.25(14); O3 C20 C19 112.73(16); C21 C20 C19 105.12(16); O3 C20 H20
110.5; C21 C20 H20 110.5; C19 C20 H20 110.5; C22 O3 C20 116.94(15); C24 C21
C16 131.05(18); C24 C21 C20 122.09(18); C16 C21 C20 106.86(16); O4 C22 O3
124.03(19); O4 C22 C23 125.4(2); O3 C22 C23 110.60(18); C22 C23 H231 109.5;
C22 C23 H232 109.5; H231 C23 H232 109.5; C22 C23 H233 109.5; H231 C23 H233
109.5; H232 C23 H233 109.5; C21 C24 C25 117.94(17); C21 C24 C26 127.15(18);
C25 C24 C26 114.84(16); O5 C25 O6 123.11(18); O5 C25 C24 125.86(17); O6 C25
C24 111.02(17); C25 O6 H60 109.5; C24 C26 C27 114.80(17); C24 C26 H261
108.6; C27 C26 H261 108.6; C24 C26 H262 108.6; C27 C26 H262 108.6; H261 C26
H262 107.5; C28 C27 C26 111.70(17); C28 C27 H271 109.3; C26 C27 H271 109.3;
C28 C27 H272 109.3; C26 C27 H272 109.3; H271 C27 H272 107.9; C29 C28 C27
125.5(2); C29 C28 H28 117.3; C27 C28 H28 117.3; C28 C29 C31 123.5(2); C28
C29 C30 121.6(2); C31 C29 C30 114.9(2); C29 C30 H301 109.5; C29 C30 H302
109.5; H301 C30 H302 109.5; C29 C30 H303 109.5; H301 C30 H303 109.5; H302
C30 H303 109.5; C29 C31 H311 109.5; C29 C31 H312 109.5; H311 C31 H312
109.5; C29 C31 H313 109.5; H311 C31 H313 109.5; H312 C31 H313 109.5;
_diffrn_measured_fraction_theta_max    0.988
_diffrn_reflns_theta_full              28.00
_diffrn_measured_fraction_theta_full   0.988
_refine_diff_density_max     0.325
_refine_diff_density_min    -0.205
_refine_diff_density_rms     0.052
CRYST1    8.984    19.004    19.004   90.00   90.00   90.00
SCALE1    0.111315  0.000000  0.000000  0.000000
SCALE2    0.000000  0.052621  0.000000  0.000000
SCALE3    0.000000  0.000000  0.052621  0.000000
```

The present invention includes embodiments, where one or more steps in a procedure are omitted, one or more additional steps are added, and/or where the order of steps is modified or reversed. All examples described herein shall be considered to be non-limiting.

It is to be understood that this invention is not limited to particular embodiments described, as such may, of course, vary. It is also to be understood that the terminology used herein is for the purpose of describing particular embodiments only, and is not intended to be limiting. Within the context of the present invention, each disclosed value may represent the upper or lower limit of a range that includes any other value. Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges and are encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which the invention belongs. Although any methods and materials similar or equivalent to those described herein can also be used in the practice or testing of the present invention, the preferred methods and materials are described. All publications mentioned herein are incorporated herein by reference to disclose and describe the methods and/or materials in the appended claims, the singular forms "a", "an", and "the" include plural referents unless the context clearly dictates otherwise. The patens and publications discussed herein are provided solely for their disclosure prior to the filing date of the present application. Nothing herein is to be construed as and admission that the present invention is not entitled to antedate such patent or publication by virtue of prior invention. Further, the dates of publication provided may be different from the actual publication dated which may need to be independently confirmed. As will be apparent to those skilled in the art upon reading this disclosure, each of the individual embodiments described and illustrated herein has discrete components and features which may be readily separated from or combined with the features of any of the other several embodiments without departing from the scope or spirit of the present invention. The figures shown herein are not necessarily drawn to scale, with some components and features being exaggerated for clarity.

EXAMPLES

Example 1

Figure 7:
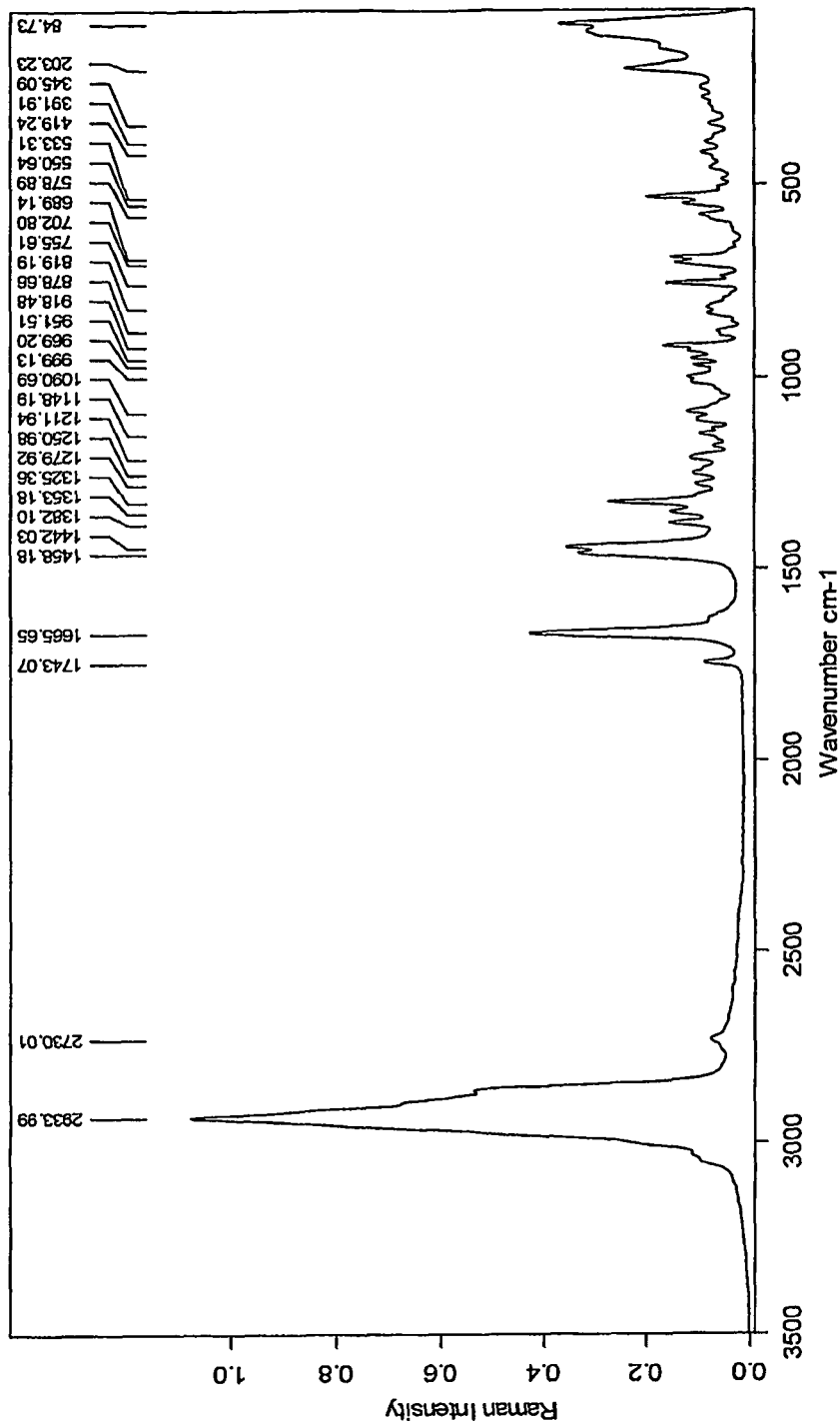
FIG. 7 is a graph showing the Raman spectrum (FT-NIR-Raman) of the crystalline fusidic acid hemihydrate. The Y-axis shows the Raman intensity and the X-axis the wavenumber (cm$^{-1}$).
Figure 8:
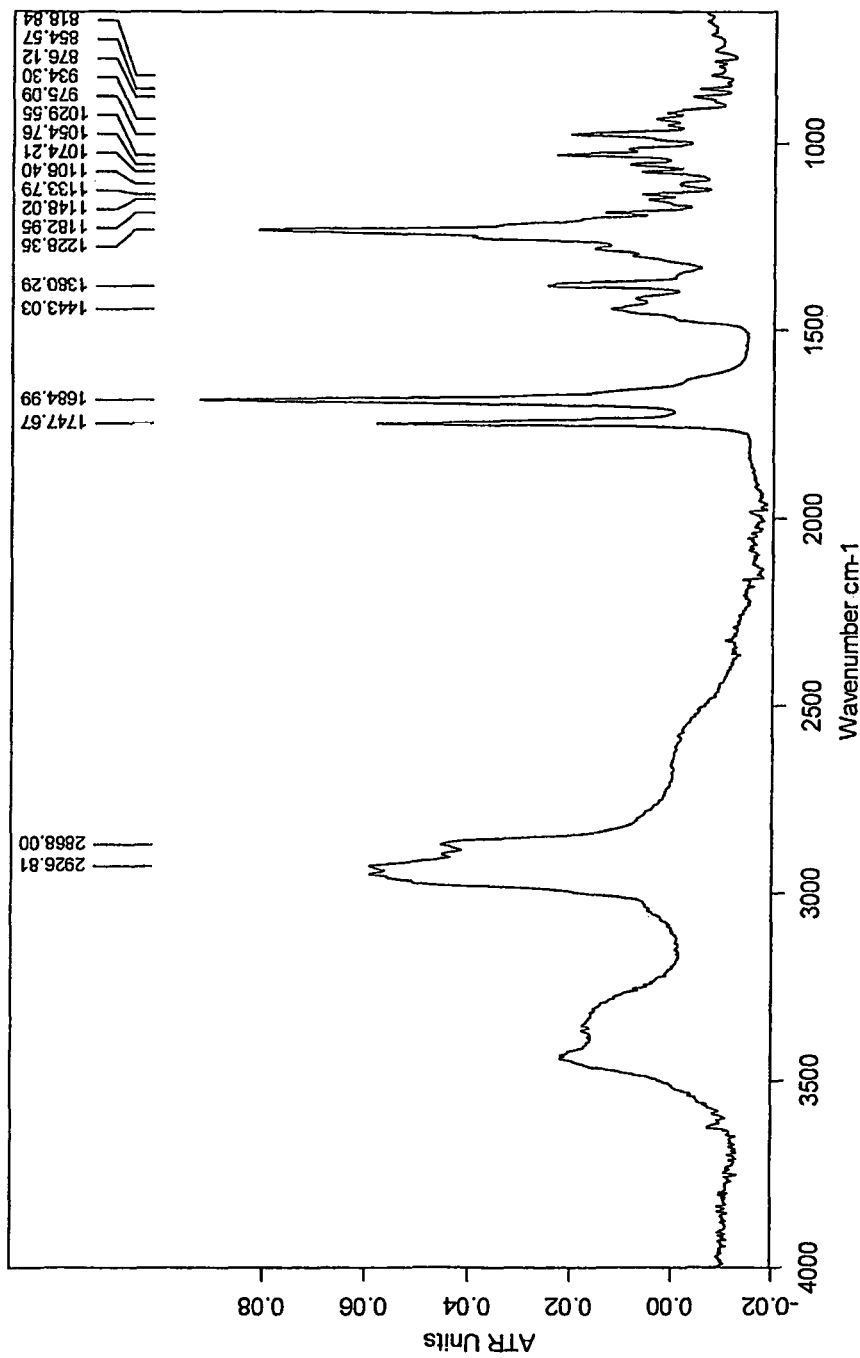
FIG. 8 is a graph showing the infrared spectrum (FTIR-ATR) of the crystalline fusidic acid hemihydrate. The Y-axis shows attenuated total reflectance units and the X-axis the wavenumber (cm$^{-1}$).
Figure 9:
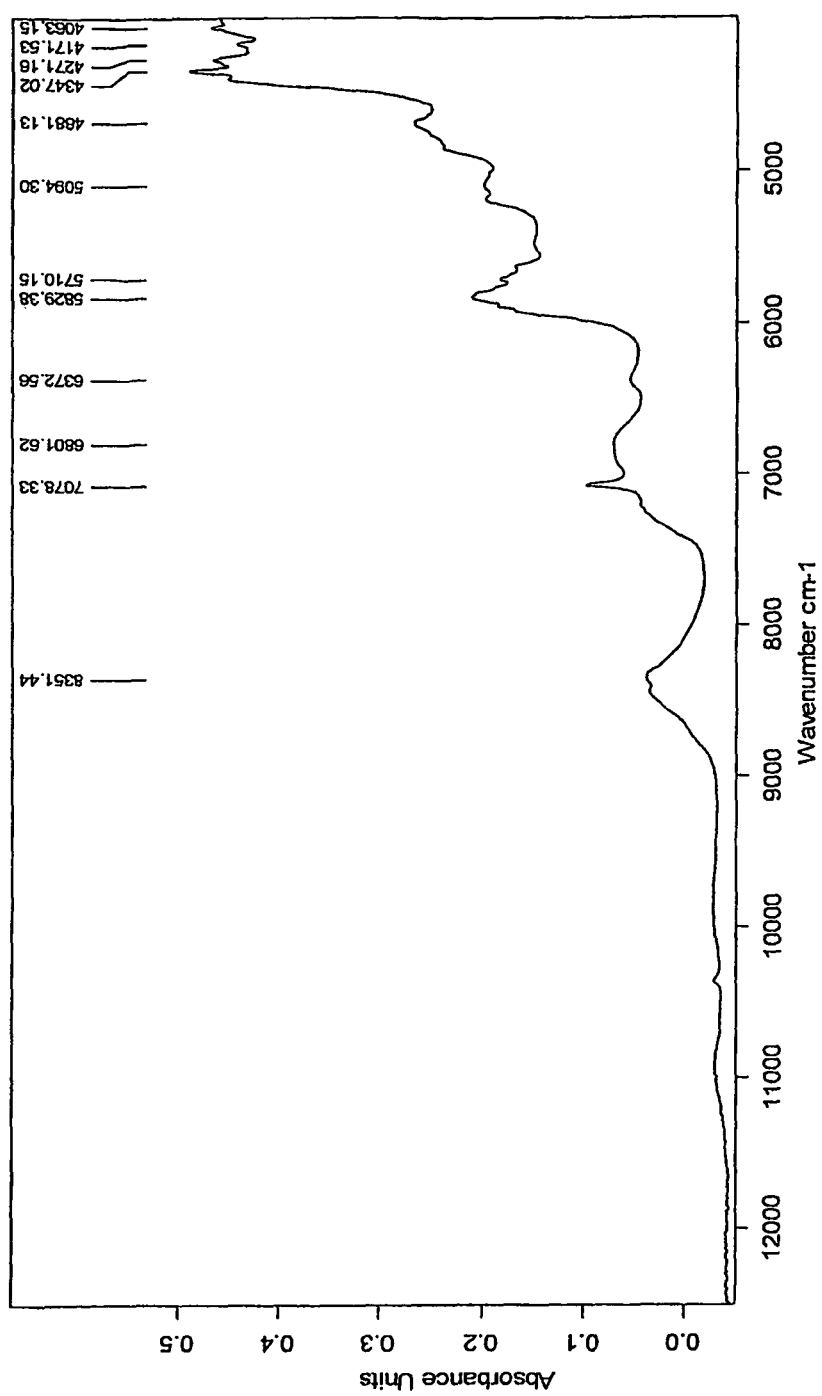
FIG. 9 is a graph showing the near infrared spectrum (FT-NIR) of the crystalline fusidic acid hemihydrate. The Y-axis shows the absorbance and the X-axis the wavenumber (cm$^{-1}$).
Figure 10:
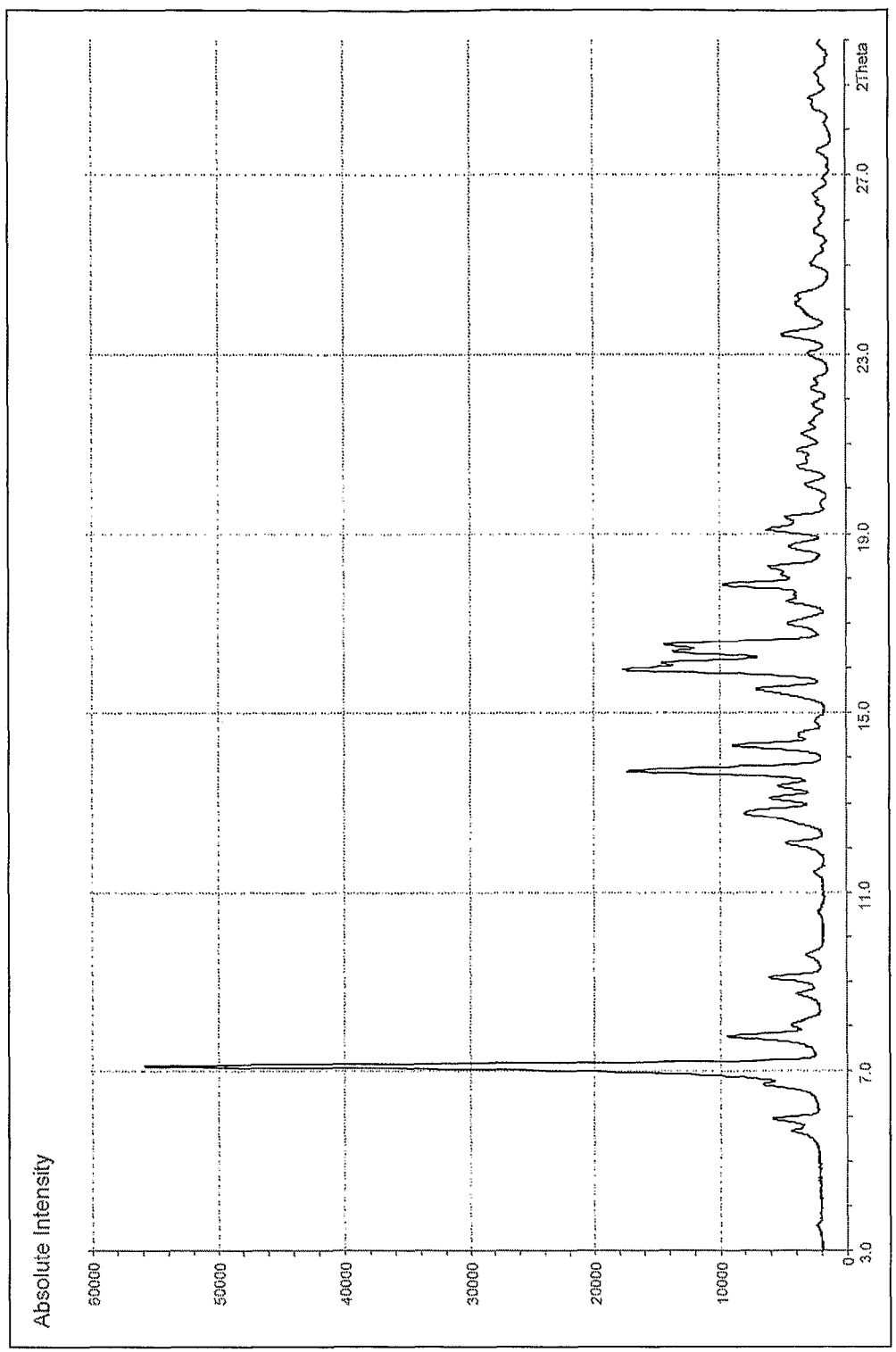
FIG. 10 shows the X-ray powder diffractogram (XRD) of the crystalline fusidic acid hemihydrate. The Y-axis shows the absolute intensity and the X-axis the angle 2θ.

Fusidic Acid Hemihydrate 17.68 kg of raw fusidic acid obtained by fermentation were dissolved in a mixture of 69.3 l of ethanol (96%) and 2.52 l acetone to provide 85.5 l of a first solution. Said first solution and 93.4 l of water were added in parallel within 17-19 minutes at ambient temperature into a container with mixing. Crystallisation was observed instantaneously after mixing of the solution with the antisolvent water. The mixture was mixed further and the crystalline fusidic acid hemihydrate was filtered off, washed with a mixture of water and ethanol (3:1, v:v) and water. A micronised sample (jet mill) of the crystals showed an endothermic peak in DSC (20° C./min) at 186° C. with an onset temperature of 183° C. The crystals were dried in vacuum at 50° C. for about 15-18 hours to yield crystalline hemihydrate characterised by exhibiting one or more of the following features l)-s), respectively:

l) a fourier transform (FT-NIR) Raman spectrum exhibiting one or more of the following intensity peaks at approximately 2934, 2730, 1743, 1666, 1458, 1442, 1382, 1353, 1325, 1280, 1251, 1212, 1148, 1091, 999, 969, 952, 918, 879, 819, 756, 703, 689, 579, 551, 533, 419, 392, 345, 203, or 85 (±3 $cm^{-1}$), respectively;

m) a fourier transform (FT-NIR) Raman spectrum substantially similar to that shown in FIG. 7;
n) an attenuated total reflectance fourier transform infrared (FTIR-ATR) spectrum exhibiting one or more of the following attenuated total reflectance peaks at approximately 3435, 2927, 2868, 1748, 1685, 1443, 1380, 1228, 1183, 1148, 1134, 1106, 1074, 1055, 1030, 975, 934, 876, 855, or 819 (±3 cm$^{-1}$), respectively, of which the following lines are the most characteristic: 3435 (broad, m), 1748 (sharp, s), 1685 (sharp, vs), 1228 (sharp, vs), 975 (sharp, m) (±3 cm$^{-1}$);
o) an attenuated total reflectance fourier transform infrared (FTIR-ATR) spectrum spectrum substantially similar to that shown in FIG. 8;
p) a near infrared (FT-NIR) spectrum exhibiting one or more of the following absorbance peaks at approximately 10358, 8351, 7078, 6801, 6373, 5829, 5710, 5094, 4681, 4347, 4271, 4172, or 4063 (±5 cm$^{-1}$), respectively;
q) a near infrared (FT-NIR) spectrum substantially similar to that shown in FIG. 9;
r) an X-ray powder diffractogram (XRD) exhibiting the following angles of reflection (2θ±0.1) at approximately 5.7, 5.9, 6.7, 7.1, 7.8, 8.0, 8.7, 9.1, 9.6, 11.5, 12.1, 12.8, 13.1, 13.4, 13.7, 14.3, 15.5, 16.0, 16.1, 16.4, 16.5, 17.0, 17.5, 17.9, 18.2, 18.7, 19.1, 19.4, 20.1, 20.9, 21.3, 21.9, 22.3, 22.5, 23.0, 23.5, 24.2, 25.1, 25.8, 26.6, or 27.5, respectively; or
s) an X-ray powder diffractogram (XRD) substantially similar to that shown in FIG. 10.

Example 2

Fusidic Acid Hemihydrate 1.64 g fusidic acid, 313 ml ethanol, 380 ml water, and 162 mg acetone were mixed and the saturated solution was filtered through a filter. 178 g fusidic acid was dissolved in 693 ml ethanol and 25 ml acetone and the solution was filtered through a filter. The first solution was poured into a 5 litre flask and stirred at 180 rpm in a water bath at temperature 30° C. The solution was seeded with 0.45 g fusidic acid hemihydrate having the characteristics as described in example 1. The second solution and water (934 ml) were added to the flask at 7-8 ml/min in parallel, making the total addition time 90 minutes. After completed addition the crystal suspension was stirred for further 30 minutes. The crystals were filtered off, and the crystals were dried at 30° C. for 18 hours under vacuum to give crystalline fusidic acid hemihydrate as described in example 1 exhibiting one or more of the following features x)-y), respectively:
x) an infrared (FT-IR) spectrum (KBr) having significant bands at approximately 1229, 1377, 1686, or 1748 (±3 cm$^{-1}$), respectively; or
y) an X-ray powder diffractogram (XRD) with characteristic intensity peaks exceeding 20% with respect to the largest peak, occurring at 2θ (±0.1) values of approximately 7.0, 13.7, or 16.0, respectively.

Example 3

Crystalline Fusidic Acid

Fusidic acid hemihydrate (0.5 g) from example 1 or 2 was added to acetonitrile (10 mL). The suspension was heated until a clear solution was obtained. The fusidic acid was crystallised by cooling to 20-25° C., collected by filtration and dried using vacuum. The crystalline fusidic acid had the NMR, Raman, IR, and XRD characteristics as shown in FIG. 1-6. Raman spectrum (FT-NIR-Raman): 3008, 2937, 2871, 1725, 1707, 1666, 1651, 1468, 1379, 1348, 1195, 1078, 1032, 972, 917, 792, 745, 696, 612, 569, 547, 527, 463, 175, 120, 86 (cm$^{-1}$); total reflectance fourier transform infrared spectrum (FTIR-ATR) attenuated total reflectance peaks: 3644, 3489, 2992, 2937, 2871, 1722, 1708, 1442, 1381, 1352, 1283, 1255, 1218, 1204, 1175, 1149, 1109, 1069, 1048, 1028, 962, 941, 917, 851, 828, 791, 750, 690, 656 (cm$^{-1}$); near infrared (FT-NIR) spectrum absorbance peaks: 10414, 8373, 7115, 6846, 6503, 5824, 4996, 4889, 4831, 4680, 4365, 4306, 4067 (cm$^{-1}$); X-ray powder diffraction (XRD) diffractogram angles of reflections (2θ): 7.22, 9.27, 9.88, 12.61, 13.05, 14.29, 14.70, 14.94, 15.39, 16.67, 17.87, 18.11, 18.51, 18.87, 19.51, 20.75, 21.83, 22.70, 23.51, 23.98, 24.37, 24.80, 25.29, 25.97, 26.60, 26.84, 27.71, 28.20, 28.89, 29.65; $^{13}$C CP/MAS solid-state NMR resonances at 173.9, 169.3, 146.1, 137.0, 133.3, 120.6, 76.2, 71.1, 69.1, 49.7, 49.4, 45.0, 39.9, 38.5, 36.9, 35.8, 34.5, 32.7, 30.9, 29.5, 28.0, 26.5, 20.7, 20.0, 18.0, or 16.9 ppm.

Example 4

Crystalline Fusidic Acid

Fusidic acid hemihydrate (1.0 g) from example 1 or 2 was added to ethyl format (10 ml). The suspension was heated until a clear solution was obtained. The fusidic acid was crystallised by cooling to 20-25° C., collected by filtration and dried using vacuum. The substance was analyzed by NIR, XRD and RAMAN and had the same characteristics as described in example 3. The crystalline fusidic acid showed an endothermic peak in DSC (20° C./min) at 191° C. with an onset temperature of 184° C. A FRIR-ATR spectrum exhibits one or more of the following characteristic attenuated total reflectance peaks at approximately 3644 (sharp, m), 3489 (m), 1722 (vs), 1708 (vs), 1381 (m), 1255 (s), 1204 (m), 962 (m) (cm$^{-1}$).

Example 5

Crystalline Fusidic Acid

Fusidic acid hemihydrate (1.0 kg) as described in example 1 was suspended in a mixture of ethanol (3.0 L) and purified water (3.0 L). The resulting suspension was heated to 50° C. and stirred for 3-4 h. The suspension was cooled on an ice bath to 0-10° C., filtrated and dried using vacuum. The isolated crystalline fusidic acid was analyzed by NIR, XRD and RAMAN and had the same characteristics as described in example 3.

Example 6

Crystalline Fusidic Acid

Fusidic acid hemihydrate (1.0 kg) as described in example 1 was suspended in ethyl format (8.0 L) and heated to 50° C. The resulting suspension was stirred for 1-2 h, cooled on an ice bath to 0-10° C., filtrated and dried using vacuum. The isolated crystalline fusidic acid was analyzed by NIR, XRD and RAMAN and had the same characteristics as described in example 3.

Example 7

Crystalline Fusidic Acid

Fusidic acid hemihydrate (10 g) as described in example 1 was suspended in ethanol:water (1:1) 50 ml and heated to 70°

C. The resulting suspension was stirred for 2-3 h, cooled on an ice bath to 0-10° C., filtrated and dried using vacuum.

The isolated crystalline fusidic acid was analyzed by NIR, XRD and RAMAN and had the same characteristics as described in example 3.

Example 8

Crystalline Fusidic Acid

Fusidic acid hemihydrate (10 g) as described in example 1 was suspended in methanol:water (1:1) 50 ml and heated to 60° C. The resulting suspension was stirred for 2-3 h, cooled on an ice bath to 0-10° C., filtrated and dried using vacuum. The isolated crystalline fusidic acid was analyzed by NIR, XRD and RAMAN and had the same characteristics as described in example 3.

Example 9

Fusidic Acid Hemihydrate

The same procedure as in example 1 may be used, except that the first solution is made starting from crystalline fusidic acid from example 7 or 8 instead of raw fusidic acid.

Example 10

Fusidic Acid Hemihydrate

The same procedure as in example 2 may be used, except that crystalline fusidic acid from example 3, 4, 5, or 6 is used for preparing the starting solution.

Figure 2:
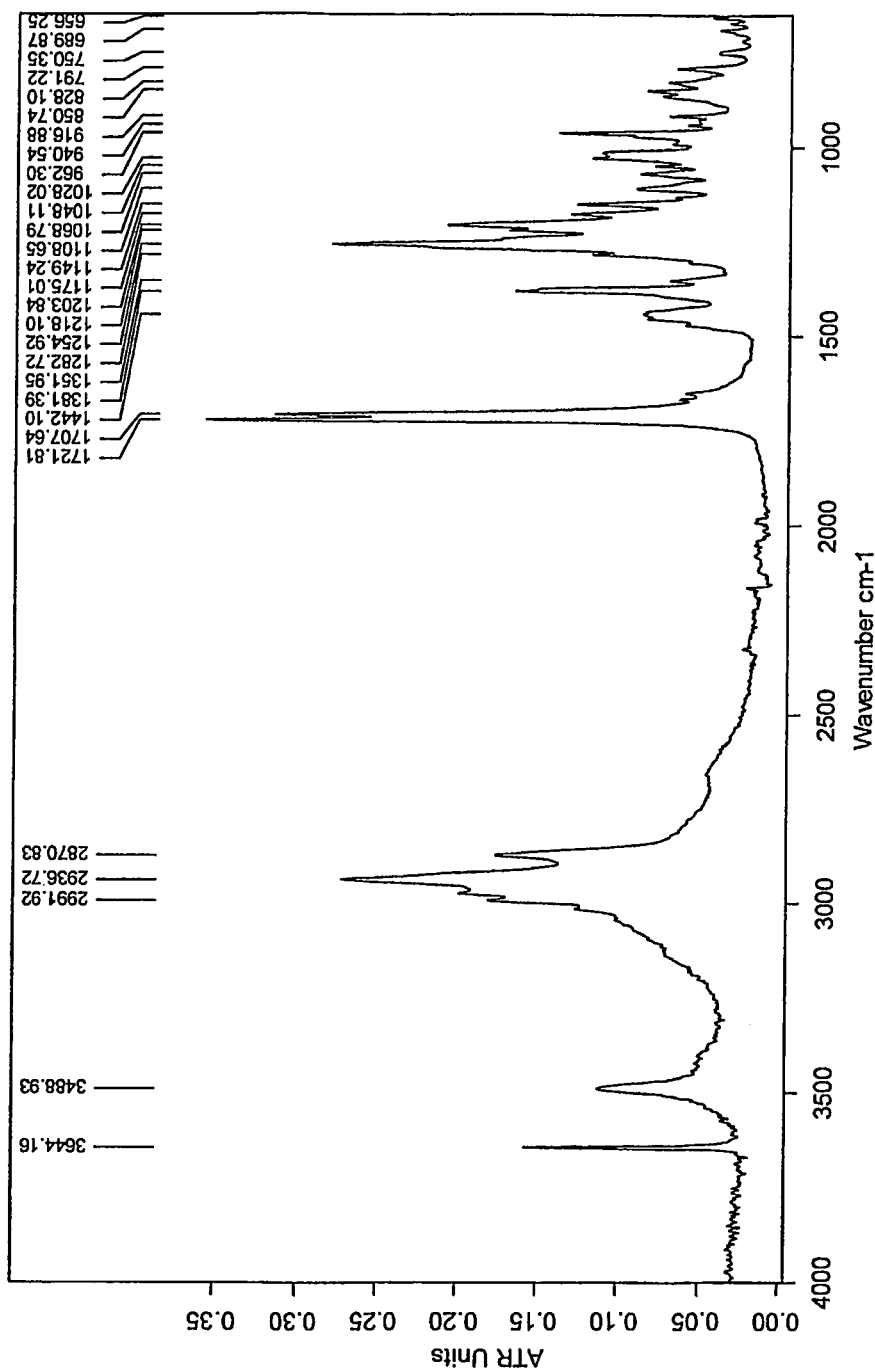
FIG. 2 is a graph showing the infrared spectrum (FTIR-ATR) of the crystalline fusidic acid of the present invention. The Y-axis shows attenuated total reflectance units and the X-axis the wavenumber (cm$^{-1}$).
Figure 3:
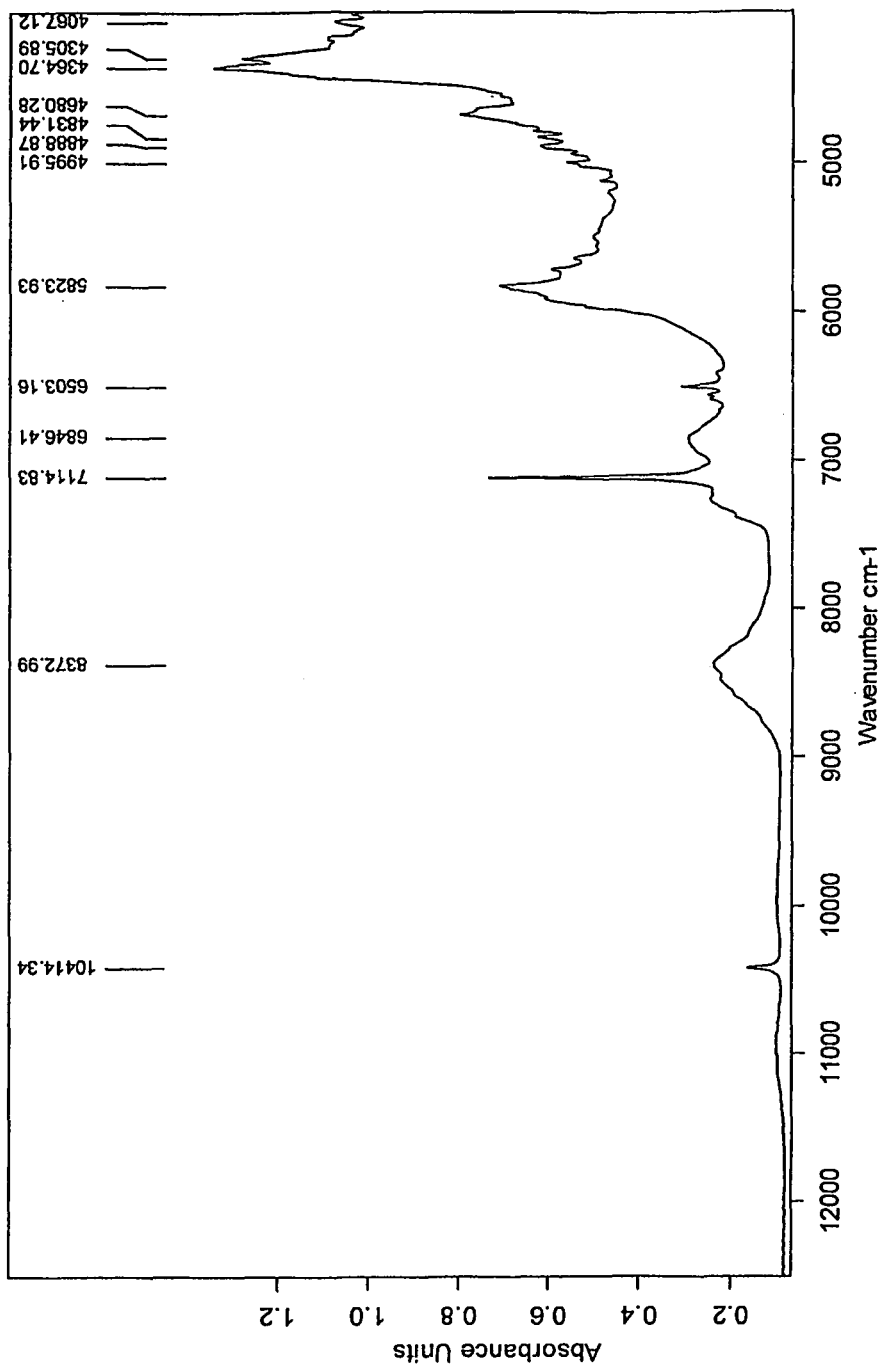
FIG. 3 is a graph showing the near infrared spectrum (FT-NIR) of the crystalline fusidic acid of the present invention. The Y-axis shows the absorbance and the X-axis the wavenumber (cm$^{-1}$).
Figure 4:
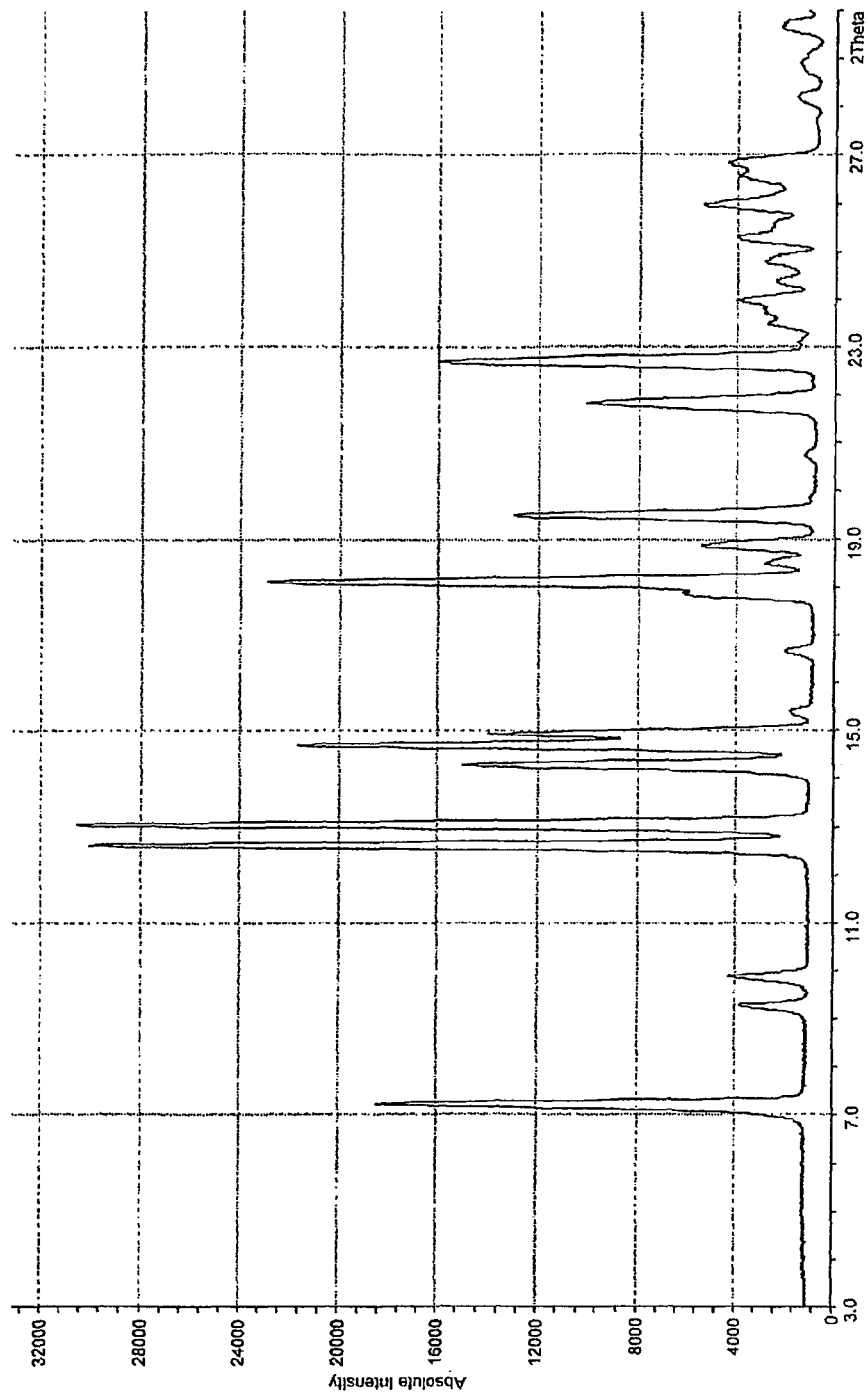
FIG. 4 shows the X-ray powder diffractogram (XRD) of the crystalline fusidic acid of the present invention. The Y-axis shows the absolute intensity and the X-axis the angle 2θ.
Figure 5:
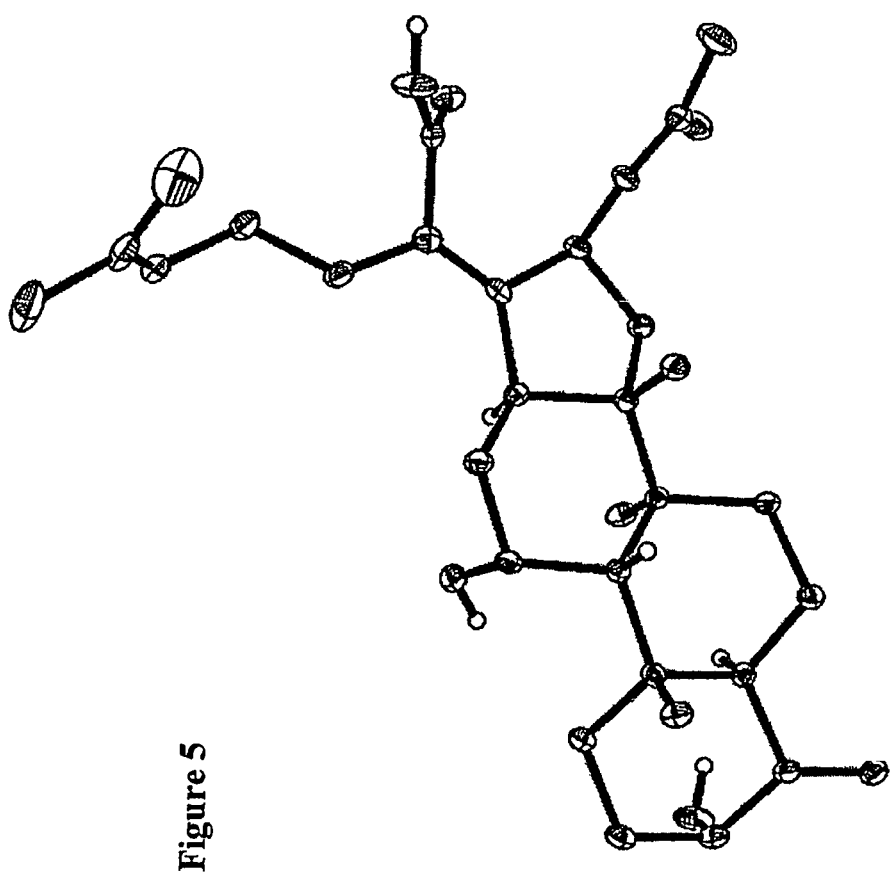
FIG. 5 shows an ORTEP plot the fusidic acid form of the present invention.
Figure 6:
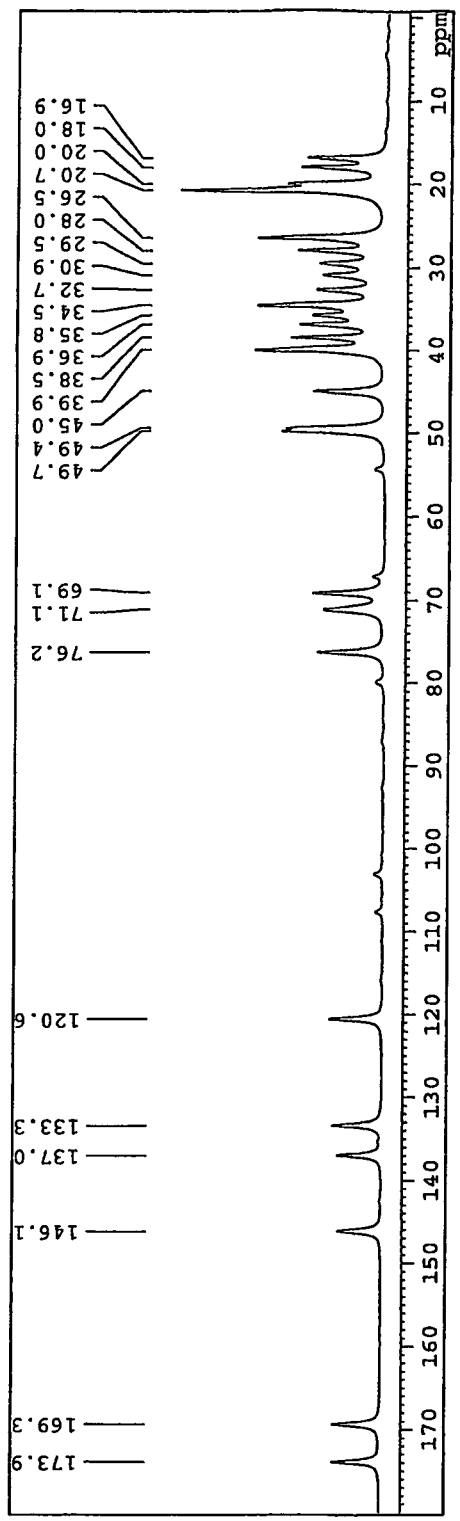
FIG. 6 shows the $^{13}$C CP/MAS solid-state NMR spectrum of the crystalline fusidic acid of the present invention.

The invention claimed is:
1. Crystalline fusidic acid characterised by:
an attenuated total reflectance fourier transform infrared (FTIR-ATR) spectrum exhibiting attenuated total reflectance peaks at approximately 3644 and or 3489 (±3 cm$^{-1}$),
exhibiting an angle of reflection (2Θ) at approximately 22.7 (±0.1) exceeding 30% with respect to the largest intensity peak in an X-ray powder diffractogram (XRD) and the absence of angles of reflection (2Θ) in the range of 10.2-12.0 (±0.1) exceeding 5% with respect to the largest intensity peak, and
an X-ray powder diffractogram (XRD) exhibiting angles of reflection (2Θ) (±0.1) at approximately 12.6, 13.1, 14.7, 14.9, 18.1, and 22.7, respectively.
2. Crystalline fusidic acid according to claim 1, further characterised by a near infrared (FT-NIR) spectrum exhibiting absorbance peaks at approximately 10414 and/or 7115 (±5 cm$^{-1}$).
3. Crystalline fusidic acid according to claim 1, further characterised by a fourier transform (FT-NIR) Raman spectrum exhibiting intensity peaks at approximately 1725, 1707, 1666, 1651 (±3 cm$^{-1}$) and the absence of an intensity peak at 1743 (±3 cm$^{-1}$) exceeding 10% with respect to the largest intensity peak.
4. Crystalline fusidic acid according to claim 1, further characterised by a $^{13}$C CP/MAS solid-state NMR spectrum exhibiting one or more of the following resonances at approximately 173.9, 137.0, or 120.6 (±0.5) ppm, respectively.
5. Crystalline fusidic acid according to claim 1, further characterised by exhibiting one or more of the following features a)-k), respectively:
a) a fourier transform (FT-NIR) Raman spectrum exhibiting the following intensity peaks at approximately 3008, 2937, 2871, 1725, 1707, 1666, 1651, 1468, 1078, 1032, 547, 463, 175, and 120 (±3 cm$^{-1}$), respectively;
b) a fourier transform (FT-NIR) Raman spectrum as shown in FIG. 1; c) an attenuated total reflectance fourier transform infrared (FTIR-ATR) spectrum exhibiting the following attenuated total reflectance peaks at approximately 3644, 3489, 1722, 1708, 1149, 962, and 828 (±3 cm$^{-1}$), respectively; d) an attenuated total reflectance fourier transform infrared (FTIR-ATR) spectrum as shown in FIG. 2;
e) a near infrared (FT-NIR) spectrum exhibiting the following absorbance peaks at approximately 10414, 7115, 6503, 4996, and 4680 (±5 cm$^{-1}$), respectively;
f) a near infrared (FT-NIR) spectrum as shown in FIG. 3;
g) an X-ray powder diffractogram (XRD) exhibiting the following angles of reflection (2Θ) (±0.1) at approximately 12.6, 13.1, 14.7, 14.9, 18.1, and 22.7 respectively;
h) an X-ray powder diffractogram (XRD) as shown in FIG. 4;
i) a $^{13}$C CP/MAS solid-state NMR spectrum exhibiting the following resonances at approximately 173.9, 169.3, 146.1, 137.0, 133.3, 120.6, 76.2, 71.1, 69.1, 49.7, 49.4, 45.0, 39.9, 38.5, 36.9, 35.8, 34.5, 32.7, 30.9, 29.5, 28.0, 26.5, 20.7, 20.0, 18.0, and 16.9 (±0.5) ppm, respectively;
j) a $^{13}$C CP/MAS solid-state NMR spectrum as shown in FIG. 6; or
k) the following single-crystal X-ray diffraction experimental data: crystal system=monoclinic and space group=P21.
6. Crystalline fusidic acid according to claim 1, further characterised by exhibiting one or more of the following features a)-k), respectively:
a) a fourier transform (FT-NIR) Raman spectrum exhibiting one or more of the following intensity peaks at approximately 3008, 2937, 2871, 1725, 1707, 1666, 1651, 1468, 1379, 1348, 1195, 1078, 1032, 972, 917, 792, 745, 696, 612, 569, 547, 527, 463, 175, 120, or 86 (±3 cm$^{-1}$), respectively;
b) a fourier transform (FT-NIR) Raman spectrum as shown in FIG. 1; c) an attenuated total reflectance fourier transform infrared (FTIR-ATR) spectrum exhibiting one or more of the following attenuated total reflectance peaks at approximately 3644, 3489, 2992, 2937, 2871, 1722, 1708, 1442, 1381, 1352, 1283, 1255, 1218, 1204, 1175, 1149, 1109, 1069, 1048, 1028, 962, 941, 917, 851, 828, 791, 750, 690, or 656 (±3 cm$^{-1}$), respectively;
d) an attenuated total reflectance fourier transform infrared (FTIR-ATR) spectrum as shown in FIG. 2;
e) a near infrared (FT-NIR) spectrum exhibiting one or more of the following absorbance peaks at approximately 10414, 8373, 7115, 6846, 6503, 5824, 4996, 4889, 4831, 4680, 4365, 4306, or 4067 (±5 cm$^{-1}$), respectively;
f) a near infrared (FT-NIR) spectrum as shown in FIG. 3;
g) an X-ray powder diffractogram (XRD) exhibiting one or more of the following angles of reflection 2Θ (±0.1) at approximately 7.2, 9.3, 9.9, 12.6, 13.1, 14.3, 14.7, 14.9, 15.4, 16.7, 17.9, 18.1, 18.5, 18.9, 19.5, 20.8, 21.8, 22.7, 23.5, 24.0, 24.4, 25.3, 26.0, 26.6, 26.8, 28.2, 28.9, or 29.7, respectively;
h) an X-ray powder diffractogram (XRD) as shown in FIG. 4;
i) a $^{13}$C CP/MAS solid-state NMR spectrum exhibiting one or more of the following resonances at approximately

173.9, 169.3, 146.1, 137.0, 133.3, 120.6, 76.2, 71.1, 69.1, 49.7, 49.4, 45.0, 39.9, 38.5, 36.9, 35.8, 34.5, 32.7, 30.9, 29.5, 28.0, 26.5, 20.7, 20.0, 18.0, or 16.9 (±0.5) ppm, respectively;

j) a $^{13}$C CP/MAS solid-state NMR spectrum as shown in FIG. 6; or k) one or more of the following single-crystal X-ray diffraction experimental data: crystal system=monoclinic, space group =P21, a[A]=12.2, b[A]=8.0, c[A]=13.9, α[°]=90 β[°]=94, γ[°]=90, cell volume [A$^3$]=1360, Z=2, respectively.

7. A mixture or formulation comprising crystalline fusidic acid according to claim 6, which further comprises crystalline fusidic acid hemihydrate.

8. A pharmaceutical composition comprising crystalline fusidic acid according to claim 1 together with a pharmaceutically acceptable excipient or vehicle.

9. A pharmaceutical composition according to claim 8 further comprising another therapeutically active compound selected from the group consisting of antibiotics and corticosteroids.

10. A method for the preparation of crystalline fusidic acid according to claim 1, said method comprising the steps of:
  a) dissolving or suspending fusidic acid hemihydrate in a solvent which is capable of dissolving said fusidic acid hemihydrate and in which the crystalline fusidic acid is essentially insoluble or sparingly soluble, optionally with heating, to give a suspension or solution;
  b) optionally heating said suspension or solution, or keeping said suspension or solution at the elevated temperature after heating in step a);
  c) optionally cooling or concentrating said suspension or solution; and
  d) isolating the crystalline fusidic acid.

11. The method according to claim 10, wherein the solvent is a water miscible organic solvent.

12. The method according to claim 10, wherein the solvent is an alkylester of formic acid.

13. The method according to claim 10, wherein the solvent is a $C_1$-$C_4$ alcohol, $C_1$-$C_4$ alkylacetate, acetonitrile, acetone, or mixtures thereof, or mixtures of said solvents with water.

14. The method according to claim 10, wherein the solvent is ethylformate, a mixture of ethanol and water, or a mixture of methanol and water.

15. The method according to claim 10, wherein the solvent is heated to about 50° C. during the step of dissolving the fusidic acid hemihydrate, and wherein the suspension or solution is kept at about 50° C. for 3-4 hours before cooling and isolation of the crystalline fusidic acid, and wherein the suspension or solution is cooled to about 0-10° C. before isolation of the crystalline fusidic acid.

16. The method according to claim 10, wherein the fusidic acid hemihydrate is completely dissolved with heating in step a) until a clear solution is obtained; optionally keeping said suspension or solution at the elevated temperature after heating in step a); followed by cooling in step c) until crystalline fusidic acid according to claim 1 precipitates.

17. The method according to claim 10, said method comprising the steps of:
  e) dissolving fusidic acid in acetonitrile, acrylonitrile, adiponitrile, benzonitrile, propanenitrile, or mixtures of said solvents, optionally with heating;
  f) cooling or concentrating of the solution obtained in step a);
  g) allowing crystalline fusidic acid to crystallise; and
  h) isolating the crystalline fusidic acid.

18. The method according to claim 17, wherein the fusidic acid in step e) is dissolved in boiling acetonitrile followed by cooling to 5-30° C. in step f).

19. A method for the preparation of crystalline fusidic acid according to claim 1, said method comprising the steps of:
  j) mixing fusidic acid with a solvent in which of crystalline fusidic acid is essentially insoluble or sparingly soluble;
  k) storing or stirring of the mixture obtained in step j), optionally with heating followed by cooling, until a suspension is obtained in which the suspended crystals essentially consist of crystalline fusidic acid; and
  i) isolating the crystalline fusidic acid from the suspension.

20. The method according to claim 19, wherein the solvent is water, ethanol, a mixture of methanol and water, acetonitrile, ethyl formate, or mixtures of said solvents.

21. Crystalline fusidic acid according to claim 1, further characterised by an X-ray powder diffractogram (XRD) exhibiting one or more of the following angles of reflection 2Θ (±0.1) of approximately 7.2, 9.3, 9.9, 12.6, 13.1, 14.3, 14.7, 14.9, 15.4, 16.7, 17.9, 18.1, 18.5, 18.9, 19.5, 20.8, 21.8, 22.7, 23.5, 24.0, 24.4, 25.3, 26.0, 26.6, 26.8, 28.2, 28.9, or 29.7, respectively.

22. Crystalline fusidic acid characterised by:
  having an X-ray powder diffractogram (XRD) as shown in FIG. 4;
  exhibiting an angle of reflection (2Θ) at approximately 22.7 (±0.1) exceeding 30% with respect to the largest intensity peak in said X-ray powder diffractogram (XRD) and the absence of angles of reflection (2Θ) in the range of 10.2-12.0 (±0.1) exceeding 5% with respect to the largest intensity peak; and
  exhibiting angles of reflection (2Θ) (±0.1) in said X-ray powder diffractogram (XRD) at approximately 12.6, 13.1, 14.7, 14.9, 18.1, and 22.7, respectively.

* * * * *